United States Patent
Lishanski et al.

(10) Patent No.: US 6,555,317 B2
(45) Date of Patent: Apr. 29, 2003

(54) DETECTION OF DIFFERENCES IN NUCLEIC ACIDS

(75) Inventors: Alla Lishanski, San Jose, CA (US); Nurith Kurn, Palo Alto, CA (US); Edwin F. Ullman, Atherton, CA (US)

(73) Assignee: Dade Behring Marburg GmbH, Marburg (DE)

( * ) Notice: Subject to any disclaimer, the term of this patent is extended or adjusted under 35 U.S.C. 154(b) by 170 days.

(21) Appl. No.: 09/732,279

(22) Filed: Dec. 7, 2000

(65) Prior Publication Data

US 2001/0014450 A1 Aug. 16, 2001

Related U.S. Application Data

(63) Continuation of application No. 09/370,919, filed on Aug. 9, 1999, now abandoned, which is a continuation of application No. 08/771,623, filed on Dec. 20, 1996, now Pat. No. 6,013,439.
(60) Provisional application No. 60/012,929, filed on Mar. 6, 1996, and provisional application No. 60/009,289, filed on Dec. 22, 1995.

(51) Int. Cl.[7] ............................. C12Q 1/68; C12P 19/34; C07H 21/02
(52) U.S. Cl. .......................... 435/6; 435/91.2; 435/808; 536/25.32
(58) Field of Search ........................... 435/6, 808, 91.2; 536/25.32

(56) References Cited

U.S. PATENT DOCUMENTS

| | | | |
|---|---|---|---|
| 4,800,159 A | * 1/1989 | Mullis et al. | ............. 435/172.3 |
| 5,561,044 A | 10/1996 | Walker et al. | ................. 435/6 |

(List continued on next page.)

FOREIGN PATENT DOCUMENTS

| | | | | |
|---|---|---|---|---|
| EP | 164876 A1 | 12/1985 | ............. | C12Q/1/68 |
| EP | 450370 A1 | 10/1991 | ............. | C12Q/1/68 |
| EP | 469 755 A1 | 2/1992 | ............. | C12P/19/34 |
| WO | WO 93/10267 | 5/1993 | ............. | C12Q/1/68 |
| WO | WO 94/03812 | 2/1994 | ............ | G01N/33/58 |

OTHER PUBLICATIONS

Panyutin et al., *The kinetics of spontaneous DNA branch migration*, Proc. Natl. Acad. Sci. USA, 91:2021–2025, 1994.

(List continued on next page.)

*Primary Examiner*—Gary Benzion
*Assistant Examiner*—Joyce Tung
(74) *Attorney, Agent, or Firm*—Patrick G. Gattari

(57) ABSTRACT

A method is disclosed for detecting the presence of a difference between two related nucleic acid sequences. In the method a complex is formed comprising both strands of each sequence. Each member of at least one pair of non-complementary strands within the complex have labels. The association of the labels as part of the complex is determined as an indication of the presence of a difference between the two related sequences. The complex generally comprises a Holliday junction. In one aspect a medium suspected of containing said two related nucleic acid sequences is treated to provide partial duplexes having non-complementary tailed portions at one end. The double stranded portions of the partial duplexes are identical except for said difference. One of the strands of one of the partial duplexes is complementary to one of the strands of the other of the partial duplexes and the other of the strands of one of the partial duplexes is complementary to the other of the strands of the other of the partial duplexes. The medium is subjected to conditions that permit the binding of the tailed portions of the partial duplexes to each other. If there is a difference in the related nucleic acid sequences, a stable complex is formed comprising a Holliday junction. If no difference exists, the complex dissociates into duplexes. A determination is made whether the stable complex is formed, the presence thereof indicating the presence of the related nucleic acid sequences. The method has application in detecting the presence of a mutation in a target sequence or in detecting the target sequence itself.

32 Claims, 7 Drawing Sheets

U.S. PATENT DOCUMENTS

| | | | |
|---|---|---|---|
| 5,624,825 A | 4/1997 | Walker et al. | 435/91.2 |
| 5,681,705 A | 10/1997 | Schram et al. | 435/6 |
| 5,736,365 A | 4/1998 | Walker et al. | 435/91.2 |

OTHER PUBLICATIONS

Cardullo et al., *Dectection of nucleic acid hybridization by nonradiative fluorescence resonance energy transfer*, Biochemistry, 85:8790–8794, 1988.

Mueller et al., *T4 Endonuclease VII Cleaves the Crossover Strands of Holliday Junction Analogs*. Proc. Natl. Acad. Sci. USA, 85:9441–9445, 1988.

Panyutin et al., *Formation of a single base mismatch impedes spontaneous DNA branch migration*, J. Mol. Biol., 230:413–424, 1993.

Birch, *Simplified Hot Start PCR*, Nature, 381:445–446, 1996.

\* cited by examiner

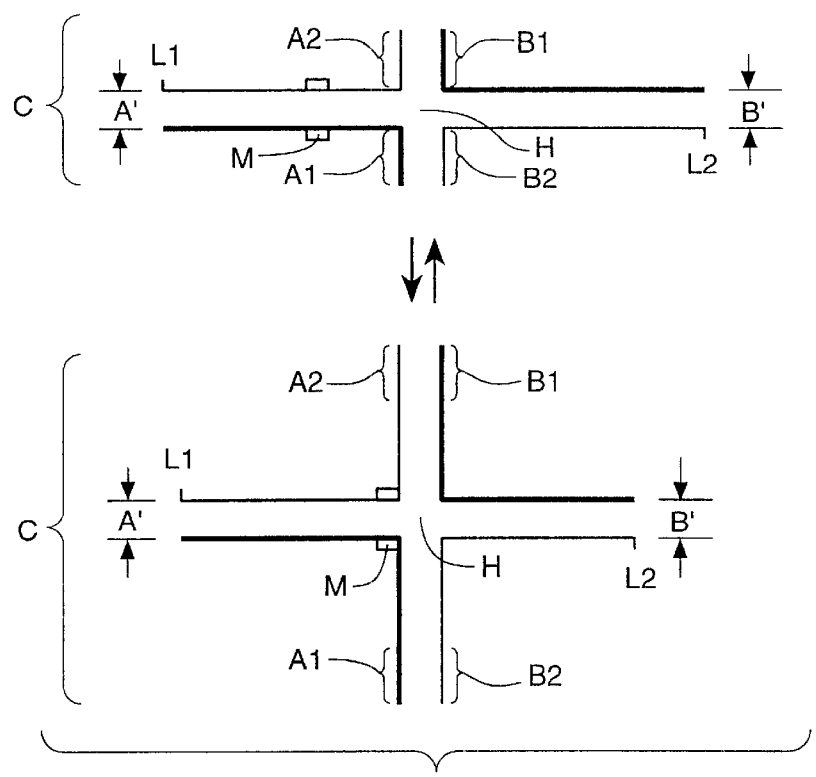
FIG._1A
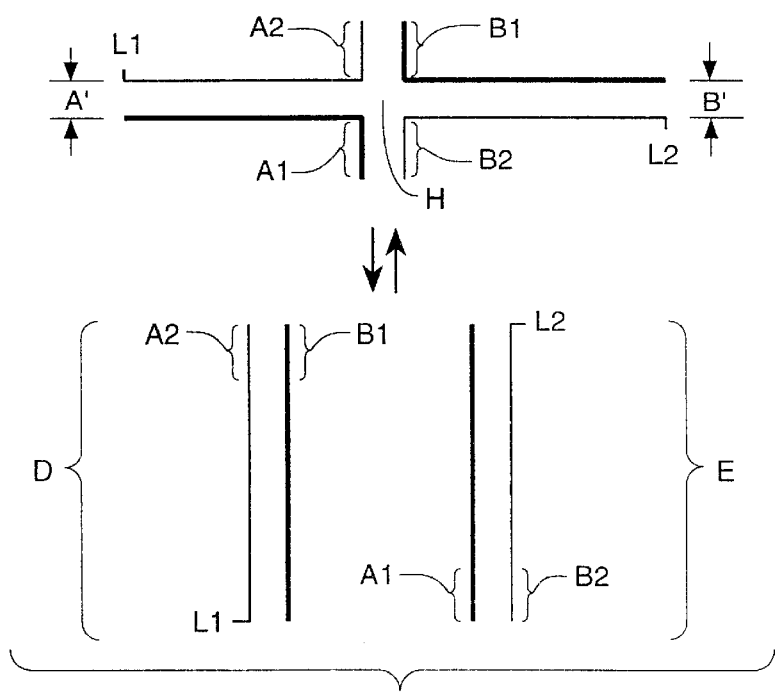
FIG._1B

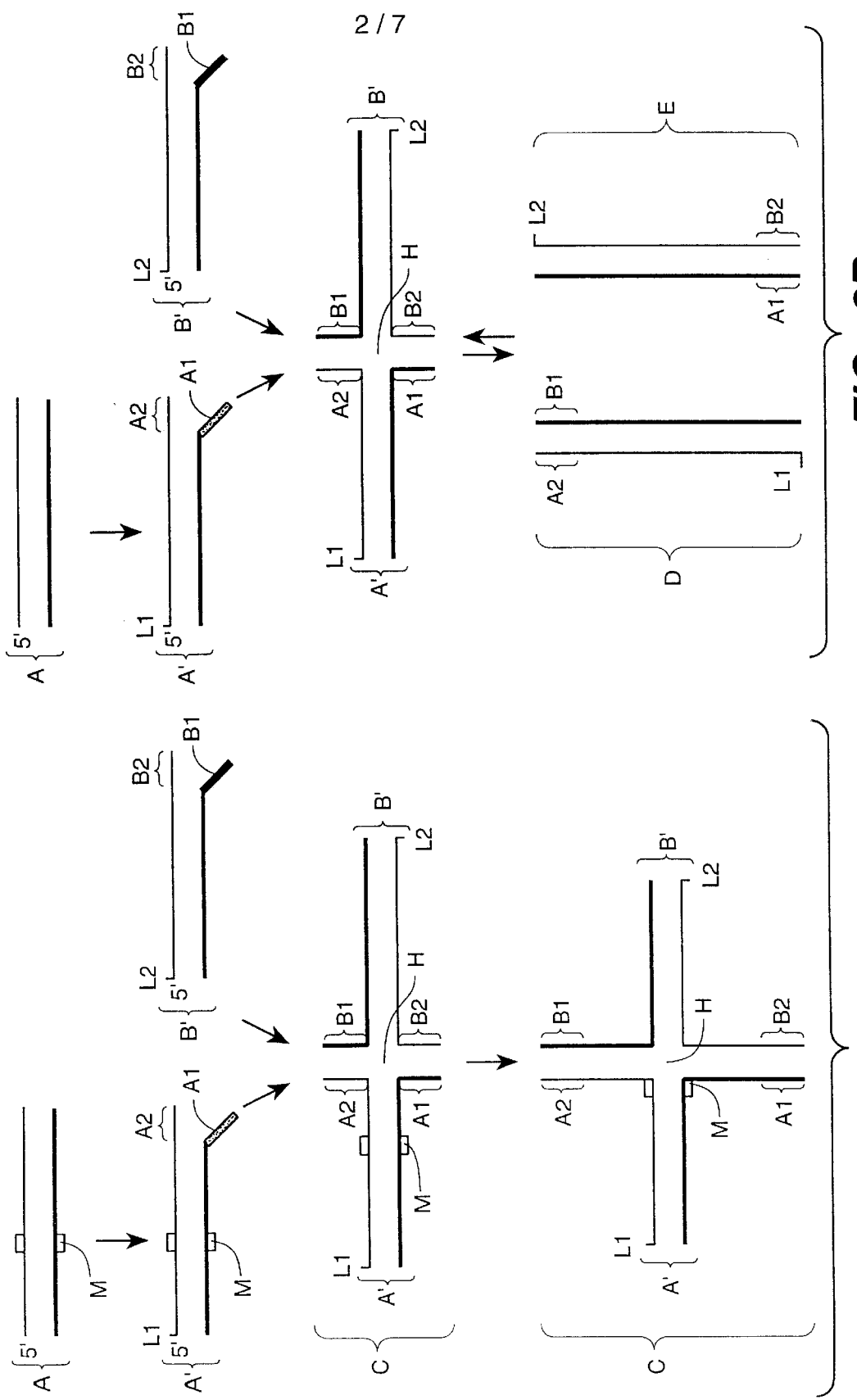
FIG._2A
FIG._2B

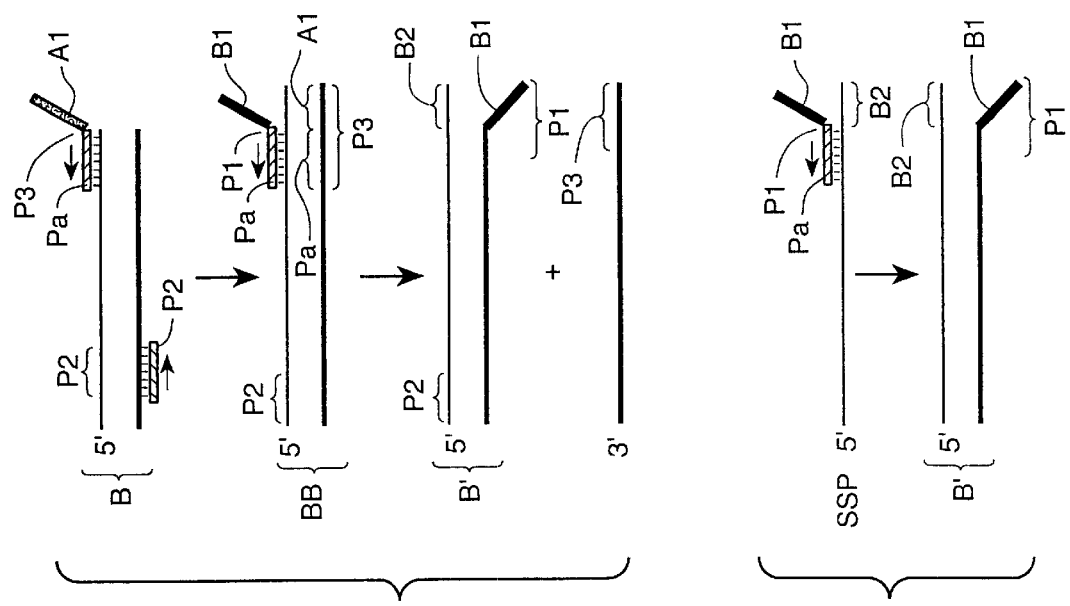
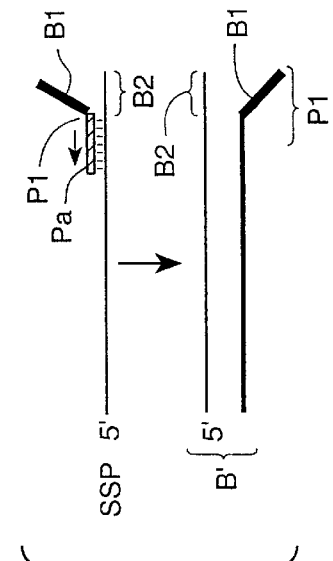
FIG._6
FIG._7
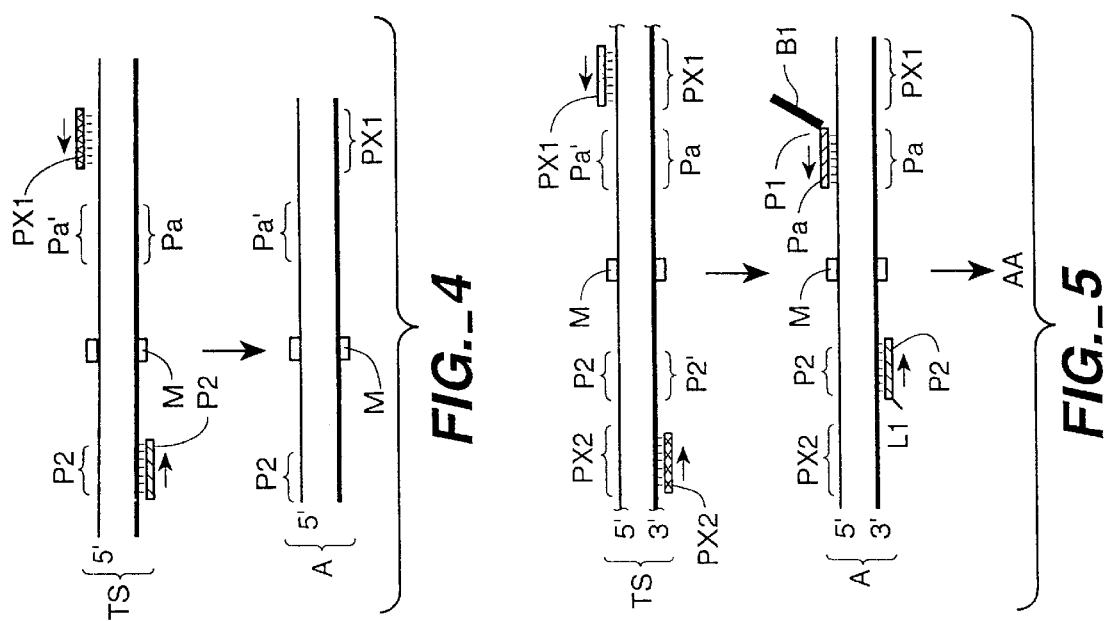
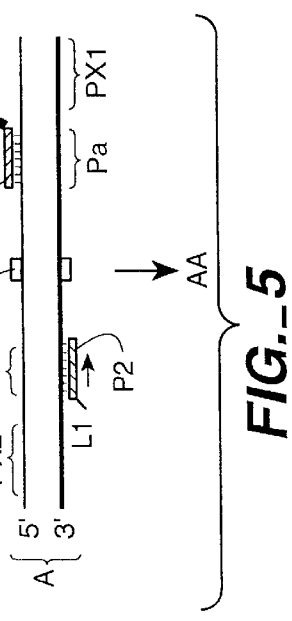
FIG._4
FIG._5

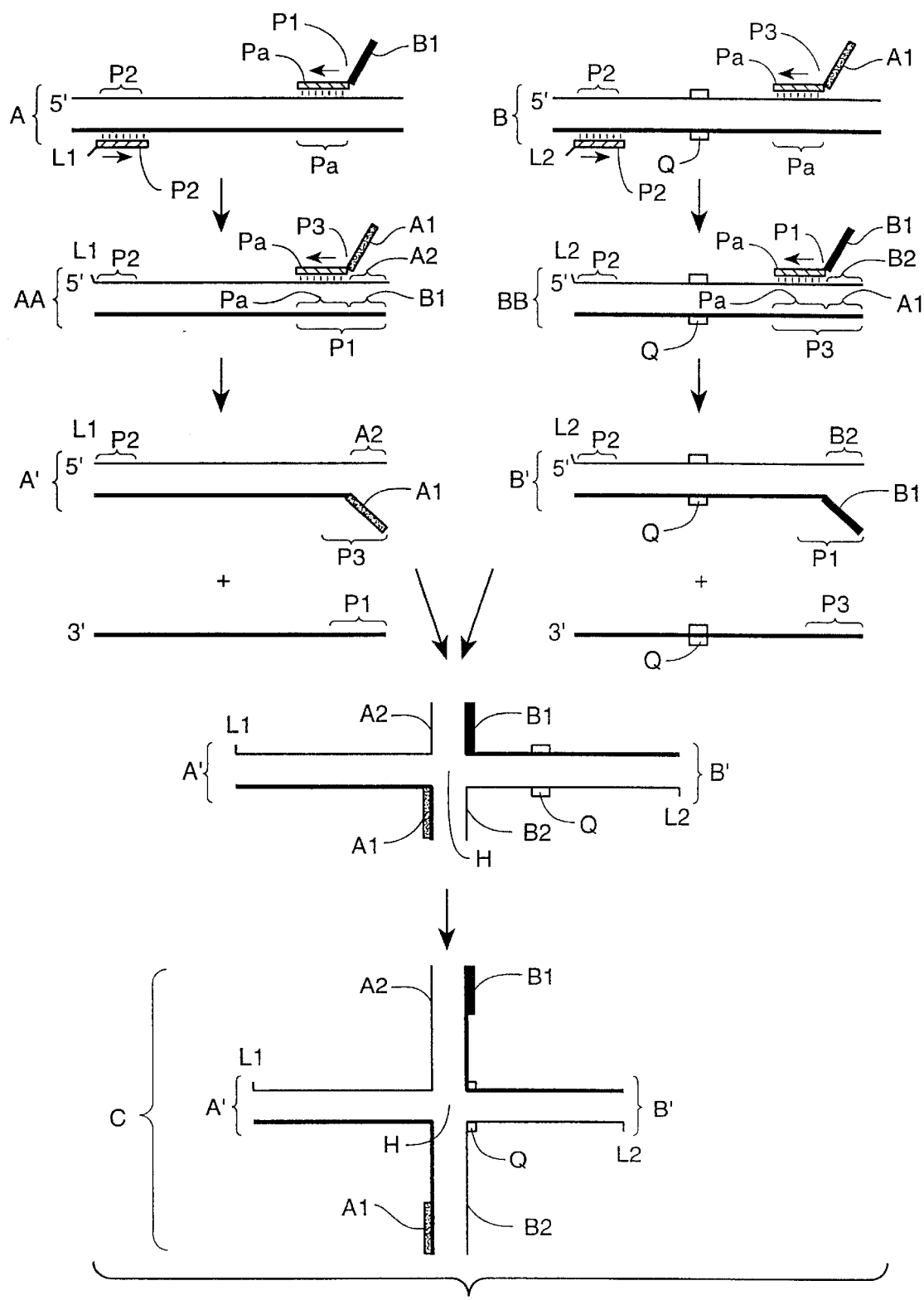
FIG._8A

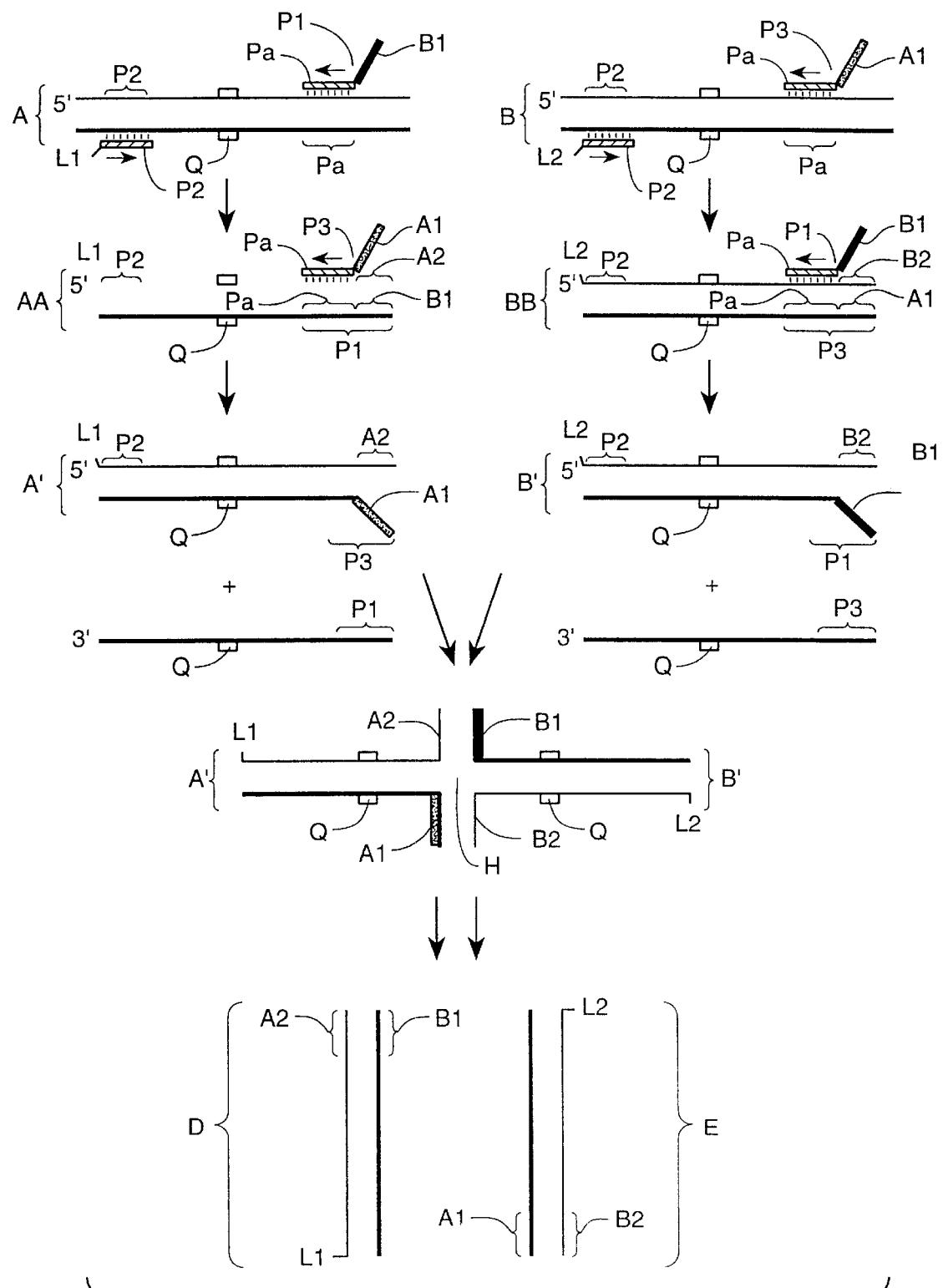
FIG._8B

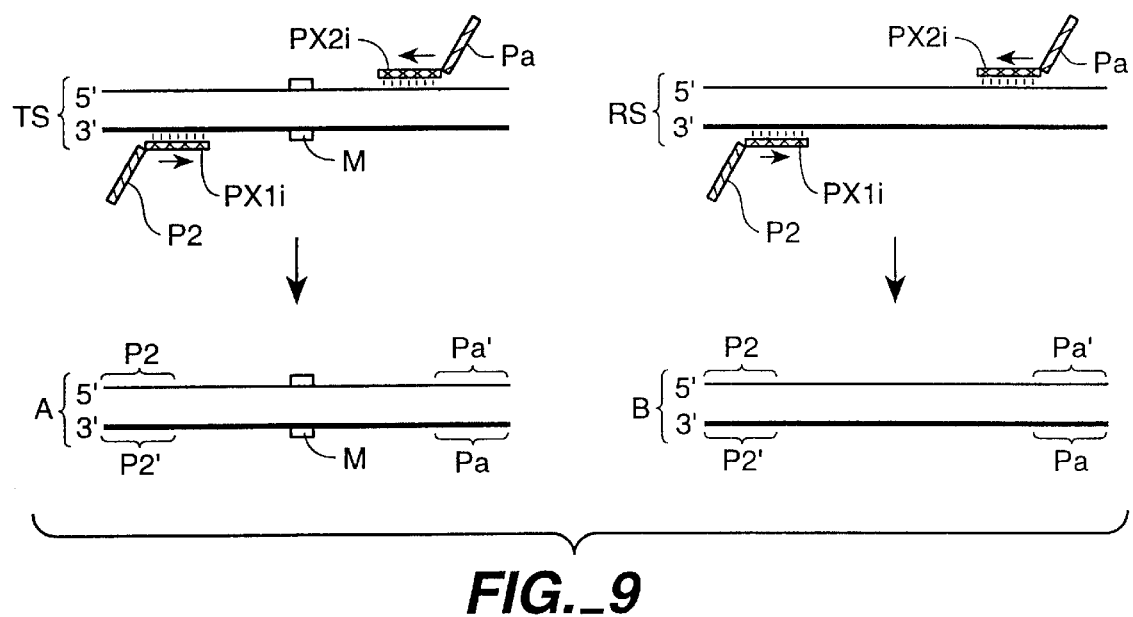
FIG._9

DETECTION OF DIFFERENCES IN NUCLEIC ACIDS

This application is a continuation U.S. patent application Ser. No. 09/370,919 filed Aug. 9, 1999, now abandoned, which a continuation of U.S. patent application Ser. No. 08/771,623 filed Dec. 20, 1996, now U.S. Pat. No. 6,013,439, which claims the benefit of U.S. Provisional Application No. 60/012,929, filed Mar. 6, 1996 and U.S. Provisional Application No. 60/009,289, filed Dec. 22, 1995.

BACKGROUND OF THE INVENTION

1. Field of the Invention

Nucleic acid hybridization has been employed for investigating the identity and establishing the presence of nucleic acids. Hybridization is based on complementary base pairing. When complementary single stranded nucleic acids are incubated together, the complementary base sequences pair to form double stranded hybrid molecules. The ability of single stranded deoxyribonucleic acid (ssDNA) or ribonucleic acid (RNA) to form a hydrogen bonded structure with a complementary nucleic acid sequence has been employed as an analytical tool in molecular biology research. The availability of radioactive nucleoside triphosphates of high specific activity and the $^{32}P$ labeling of DNA with T4 polynucleotide kinase has made it possible to identify, isolate, and characterize various nucleic acid sequences of biological interest.

Nucleic acid hybridization has great potential in diagnosing disease states associated with unique nucleic acid sequences. These unique nucleic acid sequences may result from genetic or environmental change in DNA by insertions, deletions, point mutations, or by acquiring foreign DNA or RNA by means of infection by bacteria, molds, fungi, and viruses. Nucleic acid hybridization has, until now, been employed primarily in academic and industrial molecular biology laboratories. The application of nucleic acid hybridization as a diagnostic tool in clinical medicine is limited because of the frequently very low concentrations of disease related DNA or RNA present in a patient's body fluid and the unavailability of a sufficiently sensitive method of nucleic acid hybridization analysis.

One method for detecting specific nucleic acid sequences generally involves immobilization of the target nucleic acid on a solid support such as nitrocellulose paper, cellulose paper, diazotized paper, or a nylon membrane. After the target nucleic acid is fixed on the support, the support is contacted with a suitably labeled probe nucleic acid for about two to forty-eight hours. After the above time period, the solid support is washed several times at a controlled temperature to remove unhybridized probe. The support is then dried and the hybridized material is detected by autoradiography or by spectrometric methods.

When very low concentrations must be detected, the above method is slow and labor intensive, and nonisotopic labels that are less readily detected than radiolabels are frequently not suitable.

A method for the enzymatic amplification of specific segments of DNA known as the polymerase chain reaction (PCR) method has been described. This in vitro amplification procedure is based on repeated cycles of denaturation, oligonucleotide primer annealing, and primer extension by thermophilic polymerase, resulting in the exponential increase in copies of the region flanked by the primers. The PCR primers, which anneal to opposite strands of the DNA, are positioned so that the polymerase catalyzed extension product of one primer can serve as a template strand for the other, leading to the accumulation of a discrete fragment whose length is defined by the distance between the hybridization sites on the DNA sequence complementary to the 5' ends of the oligonucleotide primers.

Other methods for amplifying nucleic acids are single primer amplification, ligase chain reaction (LCR), nucleic acid sequence based amplification (NASBA) and the Q-beta-replicase method. Regardless of the amplification used, the amplified product must be detected.

Genetic recombination involves the exchange of DNA strands between two related DNA duplexes. The branch point between two duplex DNAs that have exchanged a pair of strands is thought to be an important intermediate in homologous recombination. This branch point is otherwise referred to as the Holliday junction. Movement of the Holliday junction by branch migration can increase or decrease the amount of genetic information exchanged between homologues. In vitro strand exchange is protein mediated, unlike the spontaneous migration that occurs in vitro.

There is a great demand for simple universal high-throughput methods for detection of differences in related nucleic acid sequences regardless of the exact nature of the difference. This demand is becoming more and more urgent due to the ongoing rapid discovery of new disease related mutations brought about by the progress of the Human Genome Project. A detection method for mutations that is not dependent on the exact location of the mutation is valuable in the case of diseases that are known to result from various mutations within a given sequence. Moreover, such a method will be useful for verification of sequence homology as related to various applications in molecular biology, molecular medicine and population genetics.

Some of the current methods are either targeted for sets of known mutations, such as, for example, the Reverse Dot Blot method, or involve gel-based techniques, such as, for example, single stranded conformational polymorphism (SSCP), denaturing gradient gel electrophoresis (DGGE) or direct sequencing as well as a number of methods for the detection of heteroduplexes. Accordingly, such methods are laborious and time consuming.

Various methods for mutation detection have been developed in the recent years based on amplification technology. The detection of sequence alterations is based on one of the following principles: allele-specific hybridization, chemical modification of mismatched bases with subsequent strand cleavage, nuclease cleavage at mismatches, recognition of mismatches by specific DNA binding proteins, changes in electrophoretic mobility of mismatched duplexes in gradients of denaturing agents, conformation-induced changes in electrophoretic mobility of single-stranded DNA sometimes combined with conformation-specific nuclease cleavage. Some of these methods are too laborious and time-consuming and many depend on the nature of base alteration.

It is desirable to have a sensitive, simple, inexpensive method for detecting differences in nucleic acids such as mutations, preferably, in a homogeneous format. The method should minimize the number and complexity of steps and reagents. Such a method would be suitable for a large scale population screening.

2. Description of the Related Art

Formation of a single base mismatch that impedes spontaneous DNA branch migration is described by Panyutin, et al., (1993) *J. Mol. Biol.*, 230:413–424.

The kinetics of spontaneous DNA branch migration is discussed by Panyutin, et al., (1994) *Proc. Natl. Acad. Sci. USA,* 91: 2021–2025.

European Patent Application No. 0 450 370 A1 (Wetmur, et al.,) discloses branch migration of nucleotides.

A displacement polynucleotide assay method and polynucleotide complex reagent therefor is discussed in U.S. Pat. No. 4,766,062 (Diamond, et al.,).

A strand displacement assay and complex useful therefor is discussed in PCT application WO 94/06937 (Eadie, et al.,).

PCT application WO/86/06412 (Fritsch, et al.,) discusses process and nucleic acid construct for producing reagent complexes useful in determining target nucleotide sequences.

A process for amplifying, detecting and/or cloning nucleic acid sequences is disclosed in U.S. Pat. Nos. 4,683,195, 4,683,202, 4,800,159, 4,965,188 and 5,008,182. Sequence polymerization by polymerase chain reaction is described by Saiki, et al., (1986) *Science,* 230: 1350–1354. Primer-directed enzymatic amplification of DNA with a thermostable DNA polymerase is described by Saiki, et al, *Science* (1988) 239:487.

SUMMARY OF THE INVENTION

One method in accordance with the present invention is directed to the detection of the presence of a difference between two related nucleic acid sequences. In the method a complex is formed comprising both of the nucleic acid sequences in double stranded form. Both members of at least one pair of non-complementary strands within the complex have labels. The association of the labels as part of the complex is determined as an indication of the presence of the difference between the two related sequences. The complex may comprise a Holliday junction. The complex does not dissociate at least until detection of the labels as part of the complex has taken place and therefore, is in that sense a stable complex.

Another embodiment of the present invention is a method for detecting the presence of a difference between two related nucleic acid sequences. A medium suspected of containing two related nucleic acid sequences is treated to provide two partial duplexes each comprised of fully matched duplexes having at one end non-complementary end portions. The partial duplexes are related in that, except for the difference, one of the strands S1 of one of the partial duplexes is complementary to one of the strands S1' of the other of the partial duplexes and the other of the strands S2 of one of the partial duplexes is complementary to the other of the strands S2' of the other of the partial duplexes. The medium is subjected to conditions that permit the binding of S1 to S1' and S2 to S2', respectively. If the medium contains a difference between the related nucleic acid sequences, a stable complex is formed comprising strands S1, S1', S2 and S2'. A determination is made whether the stable complex is formed, the presence thereof indicating the presence of a difference between the related nucleic acid sequences.

Another aspect of the present invention is a method for detecting a mutation within a target nucleic acid sequence. The method comprises forming from the target sequence a tailed target partial duplex comprising a duplex of the target sequence, a label and at one end of the duplex, two non-complementary oligonucleotides, one linked to each strand. The tailed target partial duplex is provided in combination with a labeled tailed reference partial duplex lacking the mutation. The tailed reference partial duplex is comprised of two nucleic acid strands that are complementary to the strands in the tailed target partial duplex but for the possible presence of a mutation. Labels are present in non-complementary strands of the tailed target and tailed reference partial duplexes, respectively. The formation of a stable complex between the tailed partial duplexes is detected by means of the labels. The formation of the complex is directly related to the presence of the mutation.

Another aspect of the present invention is a method of detecting a mutation within a target nucleic acid sequence, which is first amplified by the polymerase chain reaction using primers P1 and P2 to produce an amplicon AA. At least one of the primers P1 and P2 contains a label and primer P1 is comprised of a 3'-end portion Pa that can hybridize with the target sequence and 5'-end portion B1 that cannot hybridize with the target sequence. A chain extension of a primer P3 along one strand of amplicon AA is carried out to produce a tailed target partial duplex A'. Primer P3 is comprised of 3'-end portion Pa and a 5'-end portion A1 that cannot hybridize to the target sequence. A reference nucleic acid sequence is also amplified, using primer P2 and primer P3, by polymerase chain reaction to produce amplicon BB. The reference sequence is identical to the target sequence but lacking a possible mutation. Generally, when primer P2 used in the amplification of the target nucleic acid sequence comprises a label, primer P2 used for amplification of the reference nucleic acid sequence comprises a label that may be the same as or different than the label of primer P2. When primer P1 used for amplification of the target nucleic acid sequence comprises a label, primer P3 comprises a label that may be the same as or different than the label of primer P1. A chain extension of primer P1 along one strand of amplicon BB is carried out to produce a tailed reference partial duplex B', which is allowed to bind to the tailed target partial duplex A'. The binding of one labeled strand to the other labeled strand as a result of the formation of a stable complex between the tailed partial duplexes is detected, the binding thereof being directly related to the presence of the mutation.

Another aspect of the present invention is a method for detecting a mutation in a nucleic acid, wherein a partial duplex A' is produced from a target nucleic acid sequence suspected of having a mutation. Partial duplex A' comprises a fully complementary double stranded nucleic acid sequence containing the target nucleic acid sequence. One strand thereof has at its 5'-end a portion A1 that does not hybridize with a corresponding portion A2 at the 3'-end of the other strand. At least one of the strands of the partial duplex A' comprises a label. A partial duplex B' is produced from a reference nucleic acid sequence that corresponds to the target nucleic acid sequence except for the mutation. Partial duplex B' comprises the double stranded nucleic acid sequence lacking the mutation wherein the strand corresponding to the strand comprising the portion A1 has at its 5'-end a portion B1 that is complementary with A2 and the other strand has at its 3'-end a portion B2 that is complementary with A1. One of the strands of partial duplex B' comprises a label wherein such strand is unable to hybridize directly to the strand of partial duplex A' that comprises a label. Partial duplexes A' and B' are subjected to conditions that permit the duplexes to hybridize to each other. If the target nucleic acid sequence having the mutation is present, a stable complex is formed comprising partial duplex A' and partial duplex B', the presence thereof indicating the presence of the nucleic acid having the mutation.

Another embodiment of the present invention is a method for detecting a mutation in a target nucleic acid. A medium containing (i) the target nucleic acid suspected of having the mutation and (ii) two primers P1 and P2, wherein P1 is extendable along one of the strands of the nucleic acid, is subjected to temperature cycling in the presence of a nucleotide polymerase and nucleoside triphosphates. P1 has a 3'-end portion Pa that does bind, and a 5'-end portion B1 that does not bind, to one of the target nucleic acid strands. P2 is extendable along the other of the strands of the target nucleic acid. In this way one extended primer is a template for the other of the primers. The medium is then combined with a primer P3, which has the 3'-end portion Pa and a 5'-end portion A1 that does not bind to the extended P2 primer. The medium is then subjected to conditions such that P3 is extended along extended primer P2 to produce only a complementary strand, and not a copy, thereof. A medium containing (i) a reference nucleic acid, which has an identical sequence to the sequence of the target nucleic acid except for the mutation and (ii) two primers P3 and P2 is subjected to temperature cycling in the presence of a nucleotide polymerase and nucleoside triphosphates. P3 is extendable along one of the strands of the reference nucleic acid, wherein Pa binds, and A1 does not bind, thereto. P2 is extendable along the other of the strands of the reference nucleic acid. Extended primer produced by the extension of one of the primers is a template for the other of the primers. The latter medium is combined with primer P1 wherein Pa binds to, and B1 does not bind to, the extended primer produced by extending P2 along the reference nucleic acid. The latter medium is subjected to conditions under which P1 is extended along extended primer P2 to produce only a complementary strand, and not a copy, of the extended primer P2. The above steps may be carried out together in the same medium or in separate reaction media and may be carried out simultaneously or wholly or partially sequentially. If the reactions are carried out in separate reaction media, the media are combined and subjected to conditions that permit the complementary strands produced in the above steps to bind to the extended primers P1 and P3, respectively, such that a stable complex is formed if a mutation is present in the target nucleic acid. A determination is made as to whether such complex is formed, the presence thereof indicating the presence of the mutation.

Another aspect of the present invention concerns a method of preparing a DNA partial duplex having a portion at an end thereof that has two predefined non-complementary single stranded sequences. A medium containing a nucleic acid is combined with a polymerase, nucleoside triphosphates and two primers. One of the primers P3 is extendable along one of the strands of the nucleic acid. P3 has a 3'-end portion Pa that does bind, and a 5'-end portion A1 that does not bind, thereto. The other of the primers P2 is extendable along the other of the strands of the nucleic acid. Extended primer produced by the extension of one of the primers is a template for the other of the primers. The medium is subjected to temperature cycling to extend the primers and then combined with a primer P1, which has 3'-end portion Pa that binds, and a 5'-end portion B1 that does not bind, to the extended primers. The medium is subjected to conditions such that P3 binds to and is extended along the extended primer P2 to produce only a complement, and not a copy, of the extended primer.

Another aspect of the present invention is a method of preparing a DNA partial homoduplex having a portion at one end that has two non-complementary single stranded sequences. A medium containing a single stranded polynucleotide is combined with a primer P1 wherein P1 has a 3'-end portion Pa that binds to a sequence that is 8 to 60 nucleotides from the 3'-end of the single stranded polynucleotide and a 8 to 60 nucleotide portion B1 that does not bind to the single stranded polynucleotide. The medium is subjected to conditions under which P1 binds to and is extended along the single stranded polynucleotide.

Another aspect of the present invention is a method for detecting a difference between two related nucleic acid sequences. A stable quadramolecular complex is formed comprising both of the nucleic acid sequences in double stranded form. The presence of the stable complex is detected by binding the complex to a receptor. The presence of the stable complex indicates the presence of a difference between the two related sequences.

The present invention also includes kits for determining a target nucleic acid sequence. A kit in accordance with the present invention comprises in packaged combination (a) a primer P2 that is extendable along one of the strands of the target nucleic acid, (b) a primer P1 comprising a 3'-end portion Pa that binds to and is extendable along the other of the strands of the target nucleic acid and a 5'-end portion B1 that does not bind to the target nucleic acid, and (c) a primer P3 comprising 3'-end portion Pa and a portion A1 that is different than B1 and does not bind to the target nucleic acid. In one aspect, the above reagents can be packaged in the same container. The kit can further include a reference nucleic acid and also may include a polymerase, nucleoside triphosphates, and a pair of primers for amplifying both the target nucleic acid and the reference nucleic acid sequences in order to increase the number of molecules for the practice of the present invention particularly for detection of a mutation in a target nucleic acid sequence.

Another aspect of the present invention is a method for detecting a target nucleic acid sequence wherein a tailed target partial duplex A' is formed from the target sequence and is comprised of a duplex of said target sequence, a label, and at one end of the duplex, two non-complementary oligonucleotides, one linked to each strand. A combination is provided comprising (i) the tailed target partial duplex A' and (ii) a tailed reference partial duplex B', which comprises a duplex of a sequence different than the target sequence, a label and, at one end of the duplex, two oligonucleotides that are complementary to the two non-complementary oligonucleotides, one linked to each strand. The formation of a complex between the partial duplexes A' and B' is detected by means of the labels, the formation thereof being directly related to the presence of the target nucleic acid sequence.

Another embodiment of the present invention is a method of detecting a target nucleic acid sequence. The method comprises amplification of the target sequence by polymerase chain reaction, using primers P1 and P2 to produce an amplicon AA. At least one of primers P1 and P2 comprises a label and primer P1 is comprised of a 3'-end portion Pa that can hybridize with the target sequence and 5'-end portion B1 that cannot hybridize with the target sequence. A primer P3 is extended by chain extension along one strand of amplicon AA to produce a tailed target partial duplex A'. Primer P3 is comprised of 3'-end portion Pa and a 5'-end portion A1 that cannot hybridize to the target sequence or its complement. A reference nucleic acid sequence different than the target nucleic acid sequence is amplified, using primer P2 and P3, by polymerase chain reaction to produce amplicon BB. When primer P2 used in the amplification of the target nucleic acid sequence comprises a label, primer P2 used for the amplification of the reference nucleic acid sequence comprises a label that may be the same or a different label. When primer P1 used in the amplification of the target nucleic acid sequence comprises a label, primer P3 comprises a label that may be the same or a different label. Primer P1 is extended by chain extension along one strand of amplicon BB to produce a tailed reference partial duplex B'. The tailed target partial duplex A' is allowed to bind to the tailed reference partial duplex B' to form a complex. The binding of one of the labels to another of the labels as a result of the formation of the complex is detected. Such binding is directly related to the presence of the target nucleic acid sequence.

Another aspect of the present invention is a method for detecting a target nucleic acid sequence wherein a partial duplex A' is produced from a target nucleic acid sequence. The duplex A' comprises a fully complementary double stranded nucleic acid sequence containing the target nucleic acid sequence wherein one strand has at its 5'-end a portion A1 that does not hybridize with a corresponding portion A2 at the 3'-end of the other strand. At least one of the strands of the partial duplex A' comprises a label. A partial duplex B' is produced from a reference nucleic acid sequence and comprises a double stranded nucleic acid sequence different from the target nucleic acid sequence. The strand corresponding to the strand comprising portion A1 has at its 5'-end a portion B1 that is complementary with A2 and the other strand has at its 3'-end a portion B2 that is complementary with A1. One of the strands of partial duplex B' comprises a label wherein such strand is unable to hybridize directly to the strand of partial duplex A' that comprises a label. Partial duplexes A' and B' are subjected to conditions that permit the duplexes to hybridize to each other to form a stable quadramolecular complex. A determination is made as to whether such complex is formed. The presence thereof indicates the presence of the target nucleic acid sequence. In an alternate embodiment the strands comprising A1 and B1 have labels instead of the strands comprising A2 and B2.

Another embodiment of the present invention is a method for detecting the presence of a difference between two related nucleic acid sequences wherein a target nucleic acid sequence and a reference nucleic acid sequence are produced from the two related nucleic acid sequences. Each respective strand of the target nucleic acid sequence and the reference nucleic acid sequence produced has a portion introduced therein that is a nucleotide sequence priming site. A partial duplex A' is produced from the target nucleic acid sequence using the nucleotide sequence priming sites. Partial duplex A' comprises a fully complementary double stranded nucleic acid sequence containing the target nucleic acid sequence wherein one strand has at its 5'-end a portion A1 that does not hybridize with a corresponding portion A2 at the 3'-end of the other strand. One of the strands of the partial duplex A' may comprise a label. A partial duplex B' is also produced from the reference nucleic acid sequence using the nucleotide sequence priming sites. Partial duplex B' comprises the double stranded nucleic acid sequence wherein the strand corresponding to the strand comprising portion A1 has at its 5'-end a portion B1 that is complementary with A2 and the other strand has at its 3'-end a portion B2 that is complementary with A1. One of the strands of the partial duplex B' may comprise a label wherein a strand comprising a label is unable to hybridize directly to a strand of the partial duplex A' when that strand comprises a label. The partial duplexes A' and B' are subjected to conditions that permit the duplexes to hybridize to each other. If the related nucleic acid sequences have a difference, a stable complex is formed comprising partial duplex A' and partial duplex B'. A determination is made as to whether a stable complex is formed, the presence thereof indicating the presence of a difference between the two related nucleic acid sequences.

Another embodiment of the present invention is a method for detecting the presence of a mutation in a target nucleic acid sequence comprising amplification of target and reference nucleic acid sequences by polymerase chain reaction using primers PX1$i$ and PX2$i$ to produce a target sequence or a reference sequence, respectively, comprising nucleotide sequence priming sites Pa' and P2'. The reference sequence is identical to the target sequence but lacks a possible mutation. The target sequence produced above is amplified by polymerase chain reaction, using primers P1 and P2, to produce an amplicon AA. One of primers P1 and P2 may comprise a label and primer P1 is comprised of a 3'-end portion Pa that can hybridize with priming site Pa' of the target sequence and 5'-end portion B1 that cannot hybridize with the target sequence. A primer P3 is extended by chain extension along one strand of amplicon AA to produce a tailed target partial duplex A'. Primer P3 is comprised of 3'-end portion Pa and a 5'-end portion A1 that cannot hybridize to the target sequence or its complement. The reference sequence produced above is amplified, using primer P2 and primer P3, by polymerase chain reaction to produce amplicon BB. Primer P2 may comprise a label when primer P2 above comprises a label and primer P3 may comprise a label when primer P1 above comprises a label. Primer P1 is extended by chain extension along one strand of amplicon BB to produce a tailed reference partial duplex B'. The tailed target partial duplex A' is allowed to bind to the tailed reference partial duplex B'. The formation of a stable complex between the tailed partial duplexes is detected, the formation thereof being directly related to the presence of the mutation.

Another embodiment of the invention is a kit as mentioned above that also includes a pair of adapter primers for amplifying the target and reference nucleic acids. One of the primers has a 3'-end portion that is hybridizable to the target and reference nucleic acids and a portion 5' thereof that is not hybridizable with the target or reference nucleic acids and is substantially identical to primer P2. The other of the primers has a 3'-end portion that is hybridizable to the target and reference nucleic acids and a portion 5' thereof that is not hybridizable with the target or reference nucleic acids and is substantially identical to the 3'-end portion Pa of primers P1 and P3. The adapter primers are usually packaged in a container separate from primers P1, P2 and P3.

BRIEF DESCRIPTION OF THE DRAWINGS

FIG. 1A is a schematic diagram of an embodiment in accordance with the present invention wherein a mutation is present in the target nucleic acid sequence and branch migration is stopped.

FIG. 1B is a schematic diagram showing complete strand exchange in the absence of a mutation in the target nucleic acid sequence, there being no difference between target and reference nucleic acid sequences.

FIG. 2A is a schematic diagram of an embodiment in accordance with the present invention wherein a mutation is present in the target nucleic acid sequence and branch migration is stopped.

FIG. 2B is a schematic diagram showing complete strand exchange in the absence of a mutation in the target nucleic acid sequence, there being no difference between target and reference nucleic acid sequences.

FIG. 4 is a schematic depiction of a preliminary FOR amplification carried out on a target nucleic acid sequence to increase the number of copies thereof.

FIG. 5 is a schematic depiction of a FOR amplification carried out in conjunction with the method of the present invention.

FIG. 6 is a schematic diagram of an aspect of a method in accordance with the present invention.

FIG. 7 is a schematic diagram of an aspect of a method in accordance with the present invention.

FIG. 8A is a schematic diagram of an embodiment in accordance with the present invention for detecting a target nucleic acid sequence using FOR wherein a mutation is present in the reference nucleic acid sequence, target sequence is present in a sample and branch migration is stopped.

FIG. 8B is a schematic diagram of an embodiment in accordance with the present invention for detecting a target nucleic acid sequence using FOR as depicted in FIG. 8A wherein no target sequence is present in a sample.

FIG. 9 is a schematic depiction of PCR amplification carried out in conjunction with the method of the present invention.

DESCRIPTION OF THE SPECIFIC EMBODIMENTS

Figure 3:
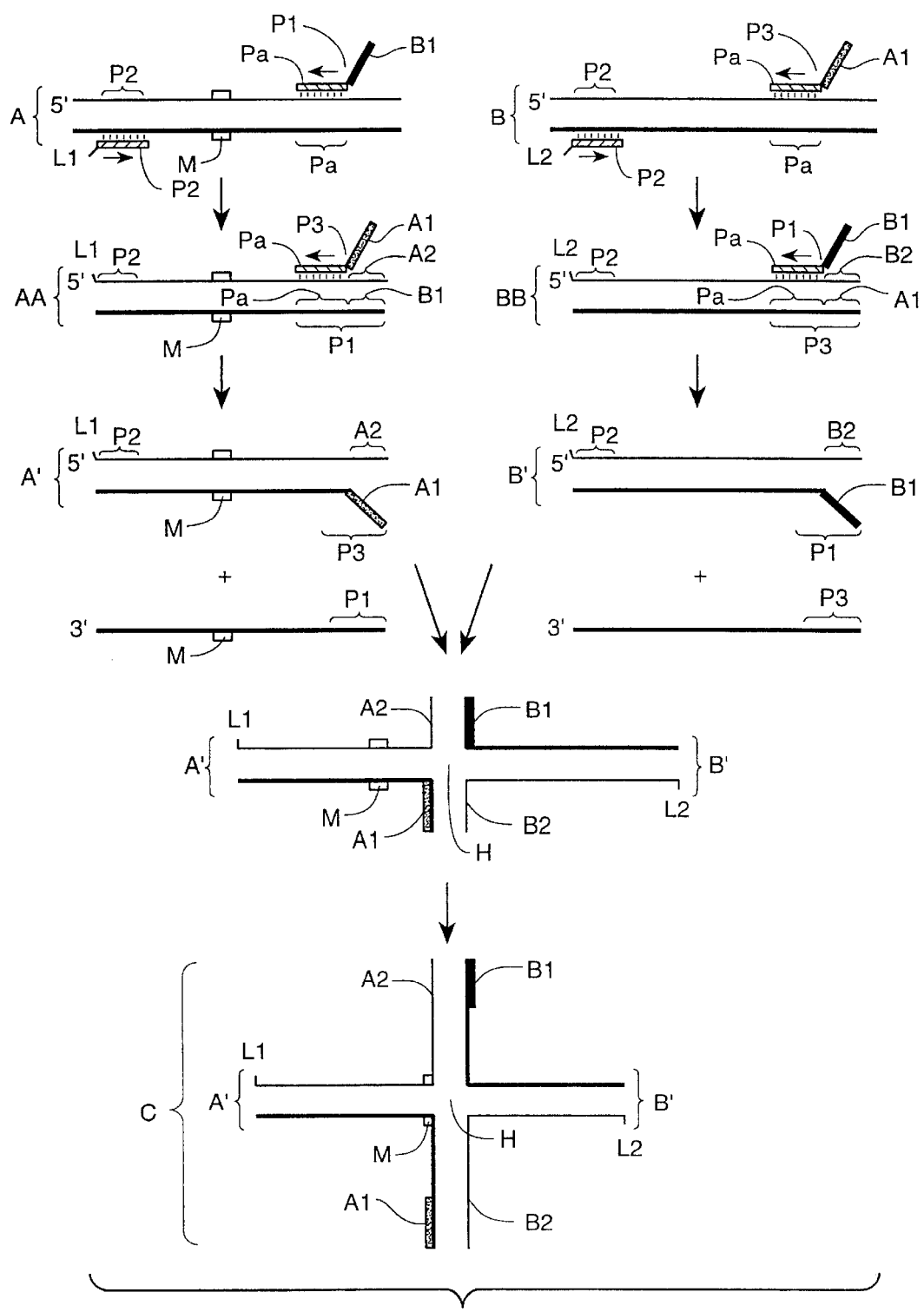
FIG. 3 is a schematic diagram of an embodiment in accordance with the present invention wherein a mutation is present in the target nucleic acid sequence and branch migration is stopped.

The present invention is universal and permits detection of any difference in two related nucleic acid sequences, whether or not such difference is known. Such differences include any mutation including single base substitution, deletion or insertion within a sequence that can be defined by a pair of primers for conducting the polymerase chain reaction. The method may be homogeneous or heterogeneous, non-radioactive, fast and amenable to automation. It is ideally suited for rapid mutation pre-screening. The invention also has application in the area of amplification by polymerase chain reaction. The present invention permits PCR and subsequent steps, such as detection of the PCR products, to be conducted without the need for additional probes in a single container without a separation step.

In one aspect the present method involves formation of a four-strand DNA structure or complex from DNA. The formation involves producing two partial duplexes by amplification by using three different primers in the polymerase chain reaction and allowing the amplified products to anneal. The complex dissociates into normal duplex structures by strand exchange by means of branch migration when the hybridized portions of each partial duplex are identical. However, where there is a difference between the two hybridized portions, the complex does not dissociate and can be detected as an indication of the presence a difference between the nucleic acids. A particularly attractive feature of the present invention is that the reactions may be carried out simultaneously in the same medium without a separation step.

Before proceeding further with a description of the specific embodiments of the present invention, a number of terms will be defined.

Nucleic acid—a compound or composition that is a polymeric nucleotide or polynucleotide. The nucleic acids include both nucleic acids and fragments thereof from any source, in purified or unpurified form including DNA (dsDNA and ssDNA) and RNA, including t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and the like. The nucleic acid can be only a minor fraction of a complex mixture such as a biological sample. The nucleic acid can be obtained from a biological sample by procedures well known in the art. Also included are genes, such as hemoglobin gene for sickle-cell anemia, cystic fibrosis gene, oncogenes, cDNA, and the like. Where the nucleic acid is RNA, it is first converted to cDNA by means of a primer and reverse transcriptase. The nucleotide polymerase used in the present invention for carrying out amplification and chain extension can have reverse transcriptase activity. Sequences of interest may be embedded in sequences of any length of the chromosome, cDNA, plasmid, etc.

Sample—the material suspected of containing the nucleic acid. Such samples include biological fluids such as blood, serum, plasma, sputum, lymphatic fluid, semen, vaginal mucus, feces, urine, spinal fluid, and the like; biological tissue such as hair and skin; and so forth. Other samples include cell cultures and the like, plants, food, forensic samples such as paper, fabrics and scrapings, water, sewage, medicinals, etc. When necessary, the sample may be pretreated with reagents to liquefy the sample and release the nucleic acids from binding substances. Such pretreatments are well known in the art.

Amplification of nucleic acids—any method that results in the formation of one or more copies of a nucleic acid (exponential amplification). One such method for enzymatic amplification of specific sequences of DNA is known as the polymerase chain reaction (PCR), as described by Saiki, et al., supra. This in vitro amplification procedure is based on repeated cycles of denaturation, oligonucleotide primer annealing, and primer extension by thermophilic template dependent polynucleotide polymerase, resulting in the exponential increase in copies of the desired sequence of the nucleic acid flanked by the primers. The two different PCR primers are designed to anneal to opposite strands of the DNA at positions that allow the polymerase catalyzed extension product of one primer to serve as a template strand for the other, leading to the accumulation of a discrete double stranded fragment whose length is defined by the distance between the 5' ends of the oligonucleotide primers. Primer length can vary from about 10 to 50 or more nucleotides and are usually selected to be at least about 15 nucleotides to ensure high specificity. The double stranded fragment that is produced is called an "amplicon" and may vary in length form as few as about 30 nucleotides to 10,000 or more.

Chain extension of nucleic acids—extension of the 3'-end of a polynucleotide in which additional nucleotides or bases are appended. Chain extension relevant to the present invention is template dependent, that is, the appended nucleotides are determined by the sequence of a template nucleic acid to which the extending chain is hybridized. The chain extension product sequence that is produced is complementary to the template sequence. Usually, chain extension is enzyme catalyzed, preferably, in the present invention, by a thermophilic DNA polymerase.

Target nucleic acid sequence—a sequence of nucleotides to be studied either for the presence of a difference from a related sequence or for the determination of its presence or absence. The target nucleic acid sequence may be double stranded or single stranded and from a natural or synthetic source. When the target nucleic acid sequence is single stranded, the method of the present invention produces a nucleic acid duplex comprising the single stranded target nucleic acid sequence.

The target sequence usually exists within a portion or all of a nucleic acid, the identity of which is known to an extent sufficient to allow preparation of various primers necessary for introducing one or more priming sites flanking the target sequence or conducting an amplification of the target sequence or a chain extension of the products of such amplification in accordance with the present invention. Accordingly, other than for the sites to which the primers bind, the identity of the target nucleic acid sequence may or may not be known. In general, in PCR, primers hybridize to, and are extended along (chain extended), at least the target sequence, and, thus, the target sequence acts as a template. The target sequence usually contains from about 30 to 20,000 or more nucleotides, more frequently, 100 to 10,000 nucleotides, preferably, 50 to 1,000 nucleotides. The target nucleic acid sequence is generally a fraction of a larger molecule or it may be substantially the entire molecule. The minimum number of nucleotides in the target sequence is selected to assure that a determination of a difference between two related nucleic acid sequences in accordance with the present invention can be achieved.

Reference nucleic acid sequence—a nucleic acid sequence that is related to the target nucleic acid in that the two sequences are identical except for the presence of a difference, such as a mutation. Where a mutation is to be detected, the reference nucleic acid sequence usually contains the normal or "wild type" sequence. In certain situations the reference nucleic acid sequence may be part of the sample as, for example, in samples from tumors, the identification of partially mutated microorganisms, or identification of heterozygous carriers of a mutation. Consequently, both the reference and the target nucleic acid sequences are subjected to similar or the same amplification conditions. As with the target nucleic acid sequence, the identity of the reference nucleic acid sequence need be known only to an extent sufficient to allow preparation of various primers necessary for introducing one or more priming sites flanking the reference sequence or conducting an amplification of the target sequence or a chain extension of the products of such amplification in accordance with the present invention. Accordingly, other that for the sites to which the primers bind, the identity of the reference nucleic acid sequence may or may not be known. The reference nucleic acid sequence may be a reagent employed in the methods in accordance with the present invention. This is particularly the situation where the present method is used in PCR amplification for detection of a target nucleic acid sequence. Depending on the method of preparation of this reagent it may or may not be necessary to know the identity of the reference nucleic acid. The reference nucleic acid reagent may be obtained form a natural source or prepared by known methods such as those described below in the definition of oligonucleotides.

Holliday junction—the branch point in a four way junction in a complex of two identical nucleic acid sequences and their complementary sequences. The junction is capable of undergoing branch migration resulting in dissociation into two double stranded sequences where sequence identity and complementarity extend to the ends of the strands.

Complex—a complex of four nucleic acid strands containing a Holliday junction, which is inhibited from dissociation into two double stranded sequences because of a difference in the sequences and their complements. Accordingly, the complex is quadramolecular.

Related nucleic acid sequences—two nucleic acid sequences are related when they contain at least 15 nucleotides at each end that are identical but have different lengths or have intervening sequences that differ by at least one nucleotide. Frequently, related nucleic acid sequences differ from each other by a single nucleotide. Such difference is referred to herein as the "difference between two related nucleic acid sequences." A difference can be produced by the substitution, deletion or insertion of any single nucleotide or a series of nucleotides within a sequence.

Mutation—a change in the sequence of nucleotides of a normally conserved nucleic acid sequence resulting in the formation of a mutant as differentiated from the normal (unaltered) or wild type sequence. Mutations can generally be divided into two general classes, namely, base-pair substitutions and frameshift mutations. The latter entail the insertion or deletion of one to several nucleotide pairs. A difference of one nucleotide can be significant as to phenotypic normality or abnormality as in the case of, for example, sickle cell anemia.

Partial duplex—a fully complementary double stranded nucleic acid sequence wherein one end thereof has non-complementary oligonucleotide sequences, one linked to each strand of the double stranded molecule, each non-complementary sequence having 8 to 60, preferably, 10 to 50, more preferably, 15 to 40, nucleotides. Thus, the partial duplex is said to be "ailed" because each strand of the duplex has a single stranded oligonucleotide chain linked thereto.

Duplex—a double stranded nucleic acid sequence wherein all of the nucleotides therein are complementary.

Oligonucleotide—a single stranded polynucleotide, usually a synthetic polynucleotide. The oligonucleotide(s) are usually comprised of a sequence of 10 to 100 nucleotides, preferably, 20 to 80 nucleotides, and more preferably, 30 to 60 nucleotides in length.

Various techniques can be employed for preparing an oligonucleotide utilized in the present invention. Such oligonucleotide can be obtained by biological synthesis or by chemical synthesis. For short sequences (up to about 100 nucleotides) chemical synthesis will frequently be more economical as compared to the biological synthesis. In addition to economy, chemical synthesis provides a convenient way of incorporating low molecular weight compounds and/or modified bases during the synthesis step. Furthermore, chemical synthesis is very flexible in the choice of length and region of the target polynucleotide binding sequence. The oligonucleotide can be synthesized by standard methods such as those used in commercial automated nucleic acid synthesizers. Chemical synthesis of DNA on a suitably modified glass or resin can result in DNA covalently attached to the surface. This may offer advantages in washing and sample handling. For longer sequences standard replication methods employed in molecular biology can be used such as the use of M13 for single stranded DNA as described by J. Messing (1983) *Methods Enzymol,* 101, 20–78.

Other methods of oligonucleotide synthesis include phosphotriester and phosphodiester methods (Narang, et al. (1979) *Meth. Enzymol* 68: 90) and synthesis on a support (Beaucage, et al. (1981) *Tetrahedron Letters* 22: 1859–1862) as well as phosphoramidate technique, Caruthers, M. H., et al., "Methods in Enzymology," Vol. 154, pp. 287–314 (1988), and others described in "Synthesis and Applications of DNA and RNA," S. A. Narang, editor, Academic Press, New York, 1987, and the references contained therein.

Oligonucleotide primer(s)—an oligonucleotide that is usually employed in a chain extension on a polynucleotide template such as in, for example, an amplification of a nucleic acid. The oligonucleotide primer is usually a synthetic oligonucleotide that is single stranded, containing a hybridizable sequence at its 3'-end that is capable of hybridizing with a defined sequence of the target or reference polynucleotide. Normally, the hybridizable sequence of the oligonucleotide primer has at least 90%, preferably 95%, most preferably 100%, complementarity to a defined sequence or primer binding site. The number of nucleotides in the hybridizable sequence of an oligonucleotide primer should be such that stringency conditions used to hybridize the oligonucleotide primer will prevent excessive random non-specific hybridization. Usually, the number of nucleotides in the hybridizable sequence of the oligonucleotide primer will be at least ten nucleotides, preferably at least 15 nucleotides and, preferably 20 to 50, nucleotides. In addition, the primer may have a sequence at its 5'-end that does not hybridize to the target or reference polynucleotides that can have 1 to 60 nucleotides, preferably, 8 to 30 polynucleotides.

Nucleoside triphosphates—nucleosides having a 5'-triphosphate substituent. The nucleosides are pentose sugar derivatives of nitrogenous bases of either purine or pyrimidine derivation, covalently bonded to the 1'-carbon of the pentose sugar, which is usually a deoxyribose or a ribose. The purine bases comprise adenine(A), guanine (G), inosine (I), and derivatives and analogs thereof. The pyrimidine bases comprise cytosine (C), thymine (T), uracil (U), and derivatives and analogs thereof. Nucleoside triphosphates include deoxyribonucleoside triphosphates such as the four common triphosphates dATP, dCTP, dGTP and dTTP and ribonucleoside triphosphates such as the four common triphosphates rATP, rCTP, rGTP and rUTP.

The term "nucleoside triphosphates" also includes derivatives and analogs thereof, which are exemplified by those derivatives that are recognized and polymerized in a similar manner to the underivatized nucleoside triphosphates. Examples of such derivatives or analogs, by way of illustration and not limitation, are those which are biotinylated, amine modified, alkylated, and the like and also include phosphorothioate, phosphite, ring atom modified derivatives, and the like.

Nucleotide—a base-sugar-phosphate combination that is the monomeric unit of nucleic acid polymers, i.e., DNA and RNA.

Modified nucleotide—is the unit in a nucleic acid polymer that results from the incorporation of a modified nucleoside triphosphate during an amplification reaction and therefore becomes part of the nucleic acid polymer.

Nucleoside—is a base-sugar combination or a nucleotide lacking a phosphate moiety.

Nucleotide polymerase—a catalyst, usually an enzyme, for forming an extension of a polynucleotide along a DNA or RNA template where the extension is complementary thereto. The nucleotide polymerase is a template dependent polynucleotide polymerase and utilizes nucleoside triphosphates as building blocks for extending the 3'-end of a polynucleotide to provide a sequence complementary with the polynucleotide template. Usually, the catalysts are enzymes, such as DNA polymerases, for example, prokaryotic DNA polymerase (I, II, or III), T4 DNA polymerase, T7 DNA polymerase, Klenow fragment, and reverse transcriptase, and are preferably thermally stable DNA polymerases such as Vent® DNA polymerase, VentR® DNA polymerase, Pfu® DNA polymerase, Taq® DNA polymerase, and the like, derived from any source such as cells, bacteria, such as *E. coli*, plants, animals, virus, thermophilic bacteria, and so forth.

Wholly or partially sequentially—when the sample and various agents utilized in the present invention are combined other than concomitantly (simultaneously), one or more may be combined with one or more of the remaining agents to form a subcombination. Subcombination and remaining agents can then be combined and can be subjected to the present method.

Hybridization (hybridizing) and binding—in the context of nucleotide sequences these terms are used interchangeably herein. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Increased stringency is achieved by elevating the temperature, increasing the ratio of cosolvents, lowering the salt concentration, and the like.

Complementary—Two sequences are complementary when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence.

Copy—means a sequence that is a direct identical copy of a single stranded polynucleotide sequence as differentiated from a sequence that is complementary to the sequence of such single stranded polynucleotide.

Conditions for extending a primer—includes a nucleotide polymerase, nucleoside triphosphates or analogs thereof capable of acting as substrates for the polymerase and other materials and conditions required for enzyme activity such as a divalent metal ion (usually magnesium), pH, ionic strength, organic solvent (such as formamide), and the like.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These may be members of an immunological pair such as antigen-antibody, or may be operator-repressor, nuclease-nucleotide, biotin-avidin, hormone—hormone receptor, IgG-protein A, DNA—DNA, DNA-RNA, and the like.

Ligand—any compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring and synthetic receptors, e.g., thyroxine binding globulin, antibodies, enzymes, Fab fragments, lectins, nucleic acids, repressors, oligonucleotides, protein A, complement component C1q, or DNA binding proteins and the like.

Small organic molecule—a compound of molecular weight less than about 1500, preferably 100 to 1000, more preferably 300 to 600 such as biotin, digoxin, fluorescein, rhodamine and other dyes, tetracycline and other protein binding molecules, and haptens, etc. The small organic molecule can provide a means for attachment of a nucleotide sequence to a label or to a support.

Support or surface—a porous or non-porous water insoluble material. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly (ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed.

Binding of sbp members to a support or surface may be accomplished by well-known techniques, commonly available in the literature. See, for example, "Immobilized Enzymes," Ichiro Chibata, Halsted Press, New York (1978) and Cuatrecasas, *J. Biol. Chem.*, 245:3059 (1970). The surface can have any one of a number of shapes, such as strip, rod, particle, including bead, and the like.

Label—a member of a signal producing system. Labels include reporter molecules that can be detected directly by virtue of generating a signal, and specific binding pair members that may be detected indirectly by subsequent binding to a cognate that contains a reporter molecule such as oligonucleotide sequences that can serve to bind a complementary sequence or a specific DNA binding protein; organic molecules such as biotin or digoxigenin that can bind respectively to streptavidin and antidigoxin antibodies, respectively; polypeptides; polysaccharides; and the like. In general, any reporter molecule that is detectable can be used. The reporter molecule can be isotopic or nonisotopic, usually non-isotopic, and can be a catalyst, such as an enzyme, dye, fluorescent molecule, chemiluminescer, coenzyme, enzyme substrate, radioactive group, a particle such as latex or carbon particle, metal sol, crystallite, liposome, cell, etc., which may or may not be further labeled with a dye, catalyst or other detectable group, and the like. The reporter group can be a fluorescent group such as fluorescein, a chemiluminescent group such as luminol, a terbium chelator such as N-(hydroxyethyl) ethylenediaminetriacetic acid that is capable of detection by delayed fluorescence, and the like.

The label is a member of a signal producing system and can generate a detectable signal either alone or together with other members of the signal producing system. As mentioned above, a reporter molecule can serve as a label and can be bound directly to a nucleotide sequence. Alternatively, the reporter molecule can bind to a nucleotide sequence by being bound to an sbp member complementary to an sbp member that comprises a label bound to a nucleotide sequence. Examples of particular labels or reporter molecules and their detection can be found in U.S. patent application Ser. No. 07/555,323 filed Jul. 19, 1990, the relevant disclosure of which is incorporated herein by reference.

Signal Producing System—the signal producing system may have one or more components, at least one component being the label. The signal producing system generates a signal that relates to the presence of a difference between the target polynucleotide sequence and the reference polynucleotide sequence. The signal producing system includes all of the reagents required to produce a measurable signal. When a reporter molecule is not conjugated to a nucleotide sequence, the reporter molecule is normally bound to an sbp member complementary to an sbp member that is bound to or part of a nucleotide sequence. Other components of the signal producing system can include substrates, enhancers, activators, chemiluminescent compounds, cofactors, inhibitors, scavengers, metal ions, specific binding substances required for binding of signal generating substances, coenzymes, substances that react with enzymic products, enzymes and catalysts, and the like. The signal producing system provides a signal detectable by external means, such as by use of electromagnetic radiation, electrochemical detection, desirably by spectrophotometric detection. The signal-producing system is described more fully in U.S. patent application Ser. No. 07/555,323, filed Jul. 19, 1990, the relevant disclosure of which is incorporated herein by reference.

Ancillary Materials—Various ancillary materials will frequently be employed in the methods and assays carried out in accordance with the present invention. For example, buffers will normally be present in the assay medium, as well as stabilizers for the assay medium and the assay components. Frequently, in addition to these additives, proteins may be included, such as albumins, organic solvents such as formamide, quaternary ammonium salts, polycations such as dextran sulfate, surfactants, particularly non-ionic surfactants, binding enhancers, e.g., polyalkylene glycols, or the like.

As mentioned above, one aspect of the present invention concerns a method for detecting the presence of a difference between two related nucleic acid sequences. In the method, if there is a difference between the two related nucleic acid sequences, a stable quadramolecular complex is formed comprising both of the nucleic acid sequences in double stranded form. Usually, the complex comprises a Holliday junction. Both members of at least one pair of non-complementary strands within the complex have labels. The association of the labels as part of the complex is determined as an indication of the presence of the difference between the two related sequences. The method may be employed for detecting the presence of a mutation in a target nucleic acid sequence or for detecting the presence of a target nucleic acid sequence.

One aspect of the invention is depicted in FIG. 1. Quadramolecular complex C comprises partial duplex A' and partial duplex B', Partial duplexes A' and B' are related in that their hybridized portions are identical except for mutation M in partial duplex A'. Additionally, partial duplex A' has a label L1, which may or may not differ from label L2 in partial duplex B'. Oligonucleotide tail A1 of partial duplex A' is hybridized to corresponding oligonucleotide tail B2 of partial duplex B' and, similarly, oligonucleotide tail A2 of partial duplex A' is hybridized to oligonucleotide tail B1 of partial duplex B'. Accordingly, complex C is quadramolecular and contains a four way junction H. Because oligonucleotide tails A1 and B1 are different, branch migration can only proceed away from these tails and then only until mutation M is reached, at which point branch migration stops (see FIG. 1A). Thus, when a mutation is present, complex C is stable and can be detected by determining whether both labels L1 and L2 have become associated. The association of the labels indicates the presence of complex C and thus the presence of mutation M in the target nucleic acid sequence. If mutation M is not present (see FIG. 1B), branch migration continues until complete strand exchange occurs and only separate duplexes D and E are present whereupon no complex C is detected.

Another embodiment in accordance with the present invention is depicted in FIG. 2. The method is for detecting a mutation within a target nucleic acid sequence A that contains mutation M. The method comprises forming from the target sequence a tailed target partial duplex A' comprised of a duplex of the target sequence, a label L1 and at one end of the duplex, two non-complementary oligonucleotides A1 and A2, one linked to each strand of duplex A'. Oligonucleotides A1 and A2 have from 8 to 60 nucleotides, preferably, 15 to 30 nucleotides. The tailed target partial duplex is provided in combination with a labeled tailed reference partial duplex B' lacking mutation M. The tailed reference partial duplex B' is comprised of two nucleic acid strands that are complementary to the strands in A' but for mutation M. Accordingly, one terminus of the tailed reference partial duplex B' has, as the end part of each strand, a sequence of nucleotides B1 and B2, respectively, that are complementary to A2 and A1, respectively, of A' and are not complementary to each other. Labels L1 and L2 are present in non-complementary strands of the tailed target and tailed reference partial duplexes A' and B', respectively, where L1 and L2 may be the same or different.

A complex C is formed as described above for FIG. 1. Oligonucleotide tail A1 of A' is hybridized to corresponding oligonucleotide tail B2 of B' and, similarly, oligonucleotide tail A2 of A' is hybridized to oligonucleotide tail B1 of B'. Because oligonucleotide tails A1 and B1 are different, branch migration can only proceed away form these tails and then only until mutation M is reached, at which point branch migration stops. Thus, when a mutation is present, complex C is stable and can be detected by determining whether both labels L1 and L2 have become associated. The association of the labels indicates the presence of complex C. The formation of complex C is directly related to the presence of the mutation. If mutation M is not present in the nucleic acid (see FIG. 2A), branch migration continues until complete strand exchange has occurred and only the separate duplexes D and E are present. In this event no complex C is detected.

Another aspect of the present invention is shown in FIG. 3, which depicts, by way of example and not limitation, the production of tailed target partial duplex A' from target nucleic acid duplex A having mutation M and the production of tailed reference partial duplex B' from reference nucleic acid duplex B. In the embodiment of FIG. 3, A is amplified by the polymerase chain reaction using primers P1 and P2 to produce an amplicon AA. Primer P2 contains a label L1 and primer P1 is comprised of a 3'-end portion Pa that can hybridize with the target sequence and 5'-end portion B1 that cannot hybridize with the target sequence. The amplification is carried out in the presence of a nucleotide polymerase and nucleoside triphosphates using temperature cycling. Amplicon AA has two strands, a labeled strand derived from primer P2 and an unlabeled strand derived from primer P1. The unlabeled strand has a 5'-end portion B1 of primer P1 and the labeled strand has a corresponding 3'-end portion A2, which is the complement of B1.

The above amplification is carried out by polymerase chain reaction (PCR) utilizing temperature cycling to achieve denaturation of duplexes, oligonucleotide primer annealing, and primer extension by thermophilic template dependent nucleotide polymerase. In conducting PCR amplification of nucleic acids, the medium is cycled between two to three temperatures. The temperatures for the present method for the amplification by PCR generally range from about 50° C. to 100° C., more usually, from about 60° C. to 95° C. Relatively low temperatures of from about 50° C. to 80° C. are employed for the hybridization steps, while denaturation is carried out at a temperature of from about 80° C. to 100° C. and extension is carried out at a temperature of from about 70° C. to 80° C., usually about 72° C. to 74° C. The amplification is conducted for a time sufficient to achieve a desired number of copies for an accurate determination of whether or not two related nucleic acids have a difference. Generally, the time period for conducting the method is from about 10 seconds to 10 minutes per cycle and any number of cycles can be used from 1 to as high as 60 or more, usually 10 to 50, frequently, 20 to 45. As a matter of convenience it is usually desirable to minimize the time period and the number of cycles. In general, the time period for a given degree of amplification can be minimized, for example, by selecting concentrations of nucleoside triphosphates sufficient to saturate the polynucleotide polymerase, by increasing the concentrations of polynucleotide polymerase and polynucleotide primer, and by using a reaction container that provides for rapid thermal equilibration. Generally, the time period for conducting the amplification in the method of the invention is from about 5 to 200 minutes.

In an example of a typical temperature cycling as may be employed, the medium is subjected to multiple temperature cycles of heating at 90° C. to 100° C. for 10 seconds to 3 minutes and cooling to 65° C. to 80° C. for a period of 10 seconds to 3 minutes.

Referring again to FIG. 3, a chain extension of primer P3 along the labeled strand of amplicon AA is then carried out to produce tailed target partial duplex A'. Primer P3 is comprised of a 3'-end portion Pa, which is identical to Pa of primer P1 and which binds to the labeled strand of AA. P3 has 5'-end portion A1 that is not complementary to amplicon AA. The chain extension is carried out in the presence of a nucleotide polymerase and nucleoside triphosphates under appropriate temperature conditions so that only the complementary strand of the labeled strand is produced and not a copy. In this particular embodiment this is achieved by removing primers P2 and P1 prior to extension of P3 in a manner as described hereinbelow. The complementary unlabeled strand of tailed target partial duplex A' has a 5'-end portion A1, which is not complementary to the 3'-end portion A2 of the labeled strand of A'. Unless the PCR reaction is carried out to produce an excess of the labeled strand, there will also be present the unlabeled strand from the amplification. This strand is not a template during chain extension to form partial duplex A'.

The conditions for carrying out the chain extension in accordance with the present invention are similar to those for the amplification described above. In general, the medium is heated to a temperature of 90° C. to 100° C. for a period of 5 to 500 seconds and then cooled to 20° C. to 80° C. for a period of 5 to 2000 seconds followed by heating to 40° C. to 80° C. for a period of 5 to 2000 seconds. Preferably, the medium is subjected to heating at 90° C. to 100° C. for a period of 10 seconds to 3 minutes, cooling to 50° C. to 65° C. for a period of 10 seconds to 2 minutes and heating to 70° C. to 80° C. for a period of 30 seconds to 5 minutes.

In carrying out the present method, an aqueous medium is employed. Other polar cosolvents may also be employed, usually oxygenated organic solvents of from 1–6, more usually from 1–4, carbon atoms, including alcohols, ethers and the like. Usually these cosolvents, if used, are present in less than about 70 weight percent, more usually in less than about 30 weight percent.

The pH for the medium is usually in the range of about 4.5 to 9.5, more usually in the range of about 5.5–8.5, and preferably in the range of about 6–8, usually about 8. In general for amplification, the pH and temperature are chosen and varied, as the case may be, so as to cause, either simultaneously or sequentially, dissociation of any internally hybridized sequences, hybridization of the oligonucleotide primer with the target nucleic acid sequence, extension of the primer, and dissociation of the extended primer. Various buffers may be used to achieve the desired pH and maintain the pH during the determination. Illustrative buffers include borate, phosphate, carbonate, Tris, barbital and the like. The particular buffer employed is not critical to this invention but in individual methods one buffer may be preferred over another. The buffer employed in the present methods normally contains magnesium ion ($Mg^{2+}$), which is commonly used with many known polymerases, although other metal ions such as manganese have also been used. Preferably, magnesium ion is used at a concentration of from about 1 to 20 mM, preferably, from about 1.5 to 10 mM, more preferably, 3–4 mM. The magnesium can be provided as a salt, for example, magnesium chloride and the like. The primary consideration is that the metal ion permit the distinction between different nucleic acids in accordance with the present invention.

The concentration of the nucleotide polymerase is usually determined empirically. Preferably, a concentration is used that is sufficient such that further increase in the concentration does not decrease the time for the amplification by over 5-fold, preferably 2-fold. The primary limiting factor generally is the cost of the reagent.

The amount of the target nucleic acid sequences that is to be examined in accordance with the present invention can be as low as one or two molecules in a sample. The priming specificity of the primers used for the detection of a difference between two related nucleic acids and other factors will be considered with regard to the need to conduct an initial amplification of the target nucleic acid. It is within the purview of the present invention for detection of a mutation to carry out a preliminary amplification reaction to increase, by a factor of $10^2$ or more, the number of molecules of the target nucleic acid sequence. The amplification can be by any convenient method such as PCR, amplification by single primer, NASBA, and so forth, but will preferably be by PCR. A PCR amplification is depicted in FIG. 4. A primer PX1 that binds upstream of the P1 and P3 binding site, depicted as Pa', and unlabeled primer P2 are utilized along with other reagents employed in accordance with known PCR amplification technology. The primers anneal to the appropriate strands of the target nucleic acid sequence TS and are extended along such strands to produce multiple copies of A. Alternatively, the number of molecules of the target nucleic acid sequence can be increased by PCR using primers P1 and P2 only or PX1 and PX2 only.

The amount of the target nucleic acid sequence to be subjected to subsequent amplification using primers in accordance with the present invention may vary from about 1 to $10^{10}$, more usually from about $10^3$ to $10^8$ molecules, preferably at least $10^{-21}$ M in the medium and may be $10^{-10}$ to $10^{-19}$M, more usually $10^{-14}$ to $10^{-19}$M.

If an initial amplification of the target nucleic acid sequence is carried to increase the number of molecules, it may be desirable, but not necessary, to remove, destroy or inactivate the primers used in the initial amplification depending on the nature of the protocol utilized. Accordingly, when the present method is carried out using step-wise addition of reagents for each separate reaction, such as, for example, in the embodiment of FIG. 3, primer P1 should be removed prior to the extension of primer P3. On the other hand, for example, in the embodiment described hereinbelow where the reactions are carried out simultaneously, it is not necessary to remove any of the primers. An example, by way of illustration and not limitation, of an approach to destroy the primers is to employ an enzyme that can digest only single stranded DNA. For example, an enzyme may be employed that has both 5' to 3' and 3' to 5' exonuclease activities, such as, e.g., exo VII. The medium is incubated at a temperature and for a period of time sufficient to digest the primers. Usually, incubation at 20° C. to 40° C. for a period of 10 to 60 minutes is sufficient for an enzyme having the above activity. The medium is next treated to inactivate the enzyme, which can be accomplished, for example, by heating for a period of time sufficient to achieve inactivation. Inactivation of the enzyme can be realized usually upon heating the medium at 90° C. to 100° C. for 0.5 to 30 minutes. Other methods of removing the primers will be suggested to those skilled in the art. It has been found, however, that removal of such primers is not necessary in carrying out the methods of the invention.

The amount of the oligonucleotide primer(s) used in the amplification reaction in the present invention will be at least as great as the number of copies desired and will usually be $10^{-9}$ to $10^{-3}$ M, preferably, $10^{-7}$ to $10^{-4}$ M. Preferably, the concentration of the oligonucleotide primer(s) is substantially in excess over, preferably at least 100 times greater than, more preferably, at least 1000 times greater than, the concentration of the target nucleic acid sequence. The concentration of the nucleoside triphosphates in the medium can vary widely; preferably, these reagents are present in an excess amount for both amplification and chain extension. The nucleoside triphosphates are usually present in $10^{-6}$ to $10^{-2}$M, preferably $10^{-5}$ to $10^{-3}$M.

The order of combining the various reagents may vary. The target nucleic acid may be combined with a pre-prepared combination of primers PX1, unlabeled P2, labeled P2, and P1, nucleoside triphosphates and nucleotide polymerase. Alternatively, the target nucleic acid, for example, can be combined with only primers PX1 and unlabeled P2 together with the nucleoside triphosphates and polymerase. After temperature cycling is carried out, the reaction mixture can be combined with the remaining primers P1 and labeled P2.

In the embodiment of FIG. 3, reference nucleic acid sequence B is in a separate medium; primer P2 and primer P3 are employed in a polymerase chain reaction to produce amplicon BB. The amplification is carried out using temperature cycling under the conditions described above in the presence of a nucleotide polymerase and nucleoside triphosphates. B is comprised of a sequence identical to A except for mutation M. Generally, primer P2 used for this amplification contains a label L2 that may be the same as or different than L1. Amplicon BB has two strands, a labeled strand derived from primer P2 and an unlabeled strand derived from primer P3. The unlabeled strand has end portion A1 of primer P3 and the labeled strand has corresponding end portion B2, which is the complement of A1.

A chain extension of primer P1 along the labeled strand of amplicon BB is carried out, under the conditions mentioned above for the chain extension of primer P3 along the labeled strand in duplex AA, to produce tailed reference partial duplex B'. As mentioned above, primer P1 is comprised of portion Pa, which binds to the labeled strand of BB and portion B1 that does not bind to amplicon BB. The chain extension is carried out in the presence of a nucleotide polymerase and nucleoside triphosphates under appropriate temperature conditions so that only the complement of the labeled strand is produced and not a copy. The extended primer P1 has a 5'-end portion B1, which is not complementary to end portion B2 of the labeled strand of B'. As can be seen, A' and B' are related in that each of their labeled strands is complementary, except for mutation M, to the unlabeled strand of the other.

The strands of partial duplexes A' and B' are allowed to bind and undergo branch migration by combining the mixtures containing partial duplexes A' and B' and incubating the combination at a temperature of 30° C. to 75° C., preferably 60° C. to 70° C., for at least one minute, preferably, 20 to 40 minutes, wherein complex C is formed as described above for FIGS. 1 and 2. Oligonucleotide tail A1 of A' is hybridized to corresponding oligonucleotide tail B2 of B' and, similarly, oligonucleotide tail A2 of A' is hybridized to oligonucleotide tail B1 of B'. Branch migration within complex C continues under the above temperature conditions with separation of the complex into duplexes D and E unless a mutation M is present, whereupon branch migration and strand dissociation is inhibited. Complex C is then detected, the presence of which is directly related to the presence of mutation M.

In the embodiment depicted in FIG. 3, labels L1 and L2 are incorporated into the partial duplexes that comprise complex C and provide a means for detection of complex C. This is by way of illustration and not limitation and other convenient methods for detecting complex C may be employed, such as the use of a receptor for the complex. In this approach there is required only one label, L1 or L2, which comprises an sbp member or a reporter molecule. A receptor for the sbp member and a receptor that can bind to complex C by virtue of a feature other than L1 or L2 can both bind to complex C and provide a means for detection.

In the embodiment of FIG. 3, the reactions are carried out independently to produce tailed partial duplexes A' and B', respectively. Then, the reaction mixtures can be combined to allow the respective strands of A' and B' to bind to one another to form complex C.

Surprisingly, however, it was discovered that the reactions of the present invention can be carried out in the same reaction medium and many or all of the reactions may be carried out simultaneously. This is a particularly attractive feature of the present invention. In this approach a combination is provided in a single medium. The combination comprises (i) a sample containing a target nucleic acid sequence suspected of having a mutation, (ii) a reference nucleic acid sequence, which may be added separately if it is not known to be present in the sample and which corresponds to the target nucleic acid lacking the mutation, which as explained above may be the wild type nucleic acid, (iii) a nucleotide polymerase, (iv) nucleoside triphosphates, and (v) primers P1, P2 and P3, wherein P2 may include primer P2 labeled with L1 and primer P2 labeled with L2, or P2 may be unlabeled and primers P1 and P3 may be labeled respectively with L1 and L2. The medium is then subjected to multiple temperature cycles of heating and cooling to simultaneously achieve all of the amplification and chain extension reactions described above for FIG. 3 except that in this embodiment there is no need to avoid making copies of any of the extended primers. Preferably, in this embodiment, each cycle includes heating the medium at 90° C. to 100° C. for 10 seconds to 3 minutes, cooling the medium to 60° C. to 70° C. for a period of 10 seconds to 3 minutes, and heating the medium at 70° C. to 75° C. for a period of 10 seconds to 3 minutes although different temperatures may be required depending on the lengths of the primer sequences. Following the above temperature cycling the medium is subjected to heating for a period of time sufficient to denature double stranded molecules, preferably, at 90° C. to 99° C. for 10 seconds to 2 minutes, and cooled to 40° C. to 80° C., preferably 60° C. to 70° C., and held at this temperature for at least one minute, preferably for 20 minutes to 2 hours.

Following cooling of the medium all possible partial and complete duplexes are formed that can form from 1) single strands that have any combination of reference or mutant sequences and 5'-ends A2 and B2, and 2) single strands having any combination of reference or mutant sequences and 5'-ends A1 or B1 wherein the strands may further be labeled with either L1 or L2 when L1 and L2 are different. Among the partial duplexes that are formed are the tailed partial duplexes A' and B', which can bind to each other to form complex C, which does not dissociate into duplexes D and E when a mutation is present. A determination of the presence of such a complex is then made to establish the presence of a mutation in the target nucleic acid sequence. When primers P1 and P3 are labeled instead of primer P2, the labels L1 and L2 in partial duplexes A' and B' are attached to tails A1 and B1, respectively, which still provides for detection of complex C when a mutation is present.

While all the steps of this determination are preferably carried out in the same medium as that used for the above reactions, some or all of the steps can be carried out wholly or partially sequentially in different media. Thus, for example, PCR amplification of target sequence A and target sequence B, each using primers P1, P2 and P3, can be conducted in separate solutions. The solution can then be combined, heated to 90° C. to 100° C. to denature strands and then incubated as before at 40° C. to 80° C. to permit formation of duplexes and complex C when a mutation is present. Detection of complex C can then be carried out directly in the combined solutions or by adding reagents required for detection or by separating the complex C, for example, on a solid surface, and detecting its presence on the surface.

When a single reaction medium is used for detecting a difference between a target and reference nucleic acid, it may be necessary to conduct an initial amplification to increase the concentration of the target nucleic acid molecules and reference nucleic acid molecules relative to that of other nucleic acids that may be present in the sample. To this end such initial amplification can be carried out using two additional primers PX1 and PX2 that bind to sites on the target and reference nucleic acids, which sites are upstream of the P2 binding site and the P1 and P3 binding site, respectively. This initial amplification can be carried out in the same medium as the above reactions. Thus, primers PX1, PX2, P1, P2 and P3 may all be combined with the target and reference sequences prior to temperature cycling. This is more readily seen in FIG. 5, which depicts the initial amplification for a mutant DNA analyte TS. Two primers PX1 and PX2 are employed and bind to sites on TS that are upstream of the sites to which primers P1 and P2, respectively, bind. These sites are indicated by Pa' and P2', respectively, in FIG. 5. The sites to which primers PX1 and PX2 bind are generally within about 0 to 500 nucleotides, preferably, about 0 to 200 nucleotides away from Pa' and P2' and may overlap partially or completely with Pa' and P2'. PX1 and PX2 are extended along their respective strands. The amplification produces multiple copies of target nucleic acid sequence A. After appropriate denaturing, primers P1 and P2 are allowed to anneal to and extend along the respective strands of A to produce multiple copies of AA. The above also occurs for the reference DNA to produce multiple copies of reference nucleic acid B, which is further amplified with primers P2 and P3 to produce multiple copies of BB.

Preferably, when an initial amplification using primers PX1 and PX2 is carried out, these primers will be designed to anneal to the target and the reference nucleic acids at a higher temperature than that for primers P1, P2 and P3, respectively. This is usually achieved by selecting PX1 and PX2 sequences that are longer or more GC rich than P2 and the Pa binding sequence in P1 and P3. The initial amplification is then carried out at temperatures that exceed the temperature required for binding P1, P2 and P3 and the subsequent amplifications to form AA and BB are carried out at lower temperatures that permit P1, P2 and P3 to bind. It is then possible to detect the difference between target and reference nucleic acid sequences by combining the sequences, primers PX1, PX2, P1, P2 and P3 wherein P2 or P1 and P3 are labeled, polynucleotide polymerase, nucleotides triphosphates, and optionally the reagents needed to detect complex C, all in one medium. The initial amplification is carried out at temperatures that permit PX1 and PX2, but not P1, P2 and P3, to bind to the target sequence whereupon sequences A and B are formed. Temperature cycling is then carried out at a lower temperature where P1, P2 and P3 can bind and be extended. The mixture is then heated to 90° C. to 100° C. to denature the duplexes and cooled to permit formation of partial duplexes AA and BB and their hybridization to form complex C. The complex can then be detected directly if all of the necessary reagents are present or detection can be carried out in a separate step. The nature of primers PX1 and PX2, as well as the appropriate temperature for binding of these primers to the target sequence, are generally determined empirically with reference to the nucleotide composition of primers P1, P2 and P3.

In another approach in accordance with the present invention, priming sites for primers P1, P2 and P3 may be introduced to the target and reference sequences, usually flanking the target or reference sequence. A PCR step is employed utilizing adapter primers consisting of two regions: a 3'-proximal region which is hybridizable to a particular priming site on the target or reference nucleic acid sequence and a 5'-proximal region which is not hybridizable to the target or reference nucleic acid sequence and has substantially the same sequence as the 3'-proximal region of a primer used in amplifications described above employed in the detection of differences between two related nucleic acids. By "substantially the same sequence" is meant that an extension product produced in an amplification using the adapter primers contains a priming site to which such primer used in amplifications described above employed in the detection of differences between two related nucleic acids can hybridize. Such adapter primers are used to prepare target and reference nucleic acid sequences having specific, universal priming sites incorporated therein, which in turn are used as templates for a universal set of primers used in the amplifications described above in accordance with the present method for detection of differences between two related nucleic acid sequences.

To this end an amplification is conducted, prior to amplifications to form AA and BB, using two additional primers PX1i and PX2i that bind to sites on the target and reference nucleic acids. This amplification may be carried out in the same or different reaction containers or different reaction media from that in which the amplifications to form AA and BB are carried out. For example, primers PX1i and PX2i are combined with the target and reference sequences, either in the same or different reaction medium, and subjected to temperature cycling. This approach is depicted in FIG. 9, which show an initial amplification for a mutant DNA analyte TS and a corresponding reference nucleic acid RS.

Two primers PX1i and PX2i are employed and bind to respective priming sites on TS and RS. PX1i has a 3'-end portion that can hybridize with the target and reference sequence and 5'-end portion Pa that cannot hybridize with the target or reference sequence. PX2i has a 3'-end portion that can hybridize with the target and reference sequence and 5'-end portion P2 that cannot hybridize with the target or reference sequence. PX1i and PX2i are extended along their respective strands. The amplification produces multiple copies of extended primers that comprise the relevant portion of the target nucleic acid sequence and reference nucleic acid sequence flanked by priming sites Pa and P2, designated A and B, respectively, in FIG. 9.

The reaction products from this initial amplification are combined with primers P1, P2 and P3 as shown in FIG. 3. Primers P1 and P2 anneal to and extend along the respective strands of A to produce multiple copies of AA. The above also occurs for the reference DNA to produce multiple copies of reference nucleic acid B, which is further amplified with primers P2 and P3 to produce multiple copies of BB. The remainder of the reactions that occur are as described above to give A' and B', which then can form complex C.

The embodiment of FIG. 9 permits the use of universal primers P1, P2 and P3. This means that one set of primers for carrying out the reactions to produce complex C can be used for the analysis of a large number of target nucleic acid sequences and corresponding reference nucleic acid sequences. Such an approach involves the use of primers PX1i and PX2i, which are designed to introduce to the target and reference sequences priming sites for universal primers P1, P2 and P3. The relationship of PX1i and PX2i are such that each contains a 5'-end portion that corresponds to the priming sequence portion, i.e., the portion of the target sequence to which the primer hybridizes, at the 3'-end of primers P1, P2 or P3 as the case may be. In the embodiment shown in FIG. 9, PX1i contains 5'-end portion P2, which results in the introduction of priming site P2' in TS to which P2 can hybridize. Primer PX2i contains 5'-end portion Pa, which results in the introduction of priming site Pa' in TS to which Pa of primers P1 and P3 can hybridize.

It is within the purview of the present invention to utilize, in conjunction with the embodiment of FIG. 9, an initial amplification as described above and exemplified in FIG. 5 to increase the concentration of the target nucleic acid molecules and reference nucleic acid molecules relative to that of other nucleic acids that may be present in the sample.

The use of universal primers allows the methods in accordance with the present invention to be carried out less expensively in some applications than a method using a different set of such primers for each target nucleic acid sequence to be analyzed. The approach has particular application in searching large, continuous stretches (tens or hundreds of kilobases) of genomic DNA for a single meaningful sequence alteration that may or may not be present. Such areas include the comparison of DNA fragments in the neighborhood of a suspected gene in both healthy and affected individuals, development of polymorphic markers for the construction of high resolution genetic maps, research applications for correlation of particular phenotypes in various model organisms with specific DNA alterations, studies of diversity within a species, and so forth.

As mentioned above, the identity of the target nucleic acid sequence does not need to be known except to the extent to allow preparation of the necessary primers for carrying out the above reactions. The present invention permits the determination of the presence or absence of a mutation in a nucleic acid in a sample without the need to fully identify the sequence of the nucleic acid. Accordingly, one is able to determine the presence of a mutation in a nucleic acid between two sequences of nucleotides for which primers can be made.

In the present invention one means of detecting the quadramolecular complex involves the use of two labels on non-complementary strands. The labels become associated by virtue of both being present in the quadramolecular complex if a difference is present between the related sequences. Detection of the two labels in the complex provides for detection of the complex. Generally, the association of the labels within the complex is detected. This association may be detected in many ways. For example, one of the labels can be an sbp member and a complementary sbp member is provided attached to a support. Upon the binding of the complementary sbp members to one another, the complex becomes bound to the support and is separated from the reaction medium. The other label employed is a reporter molecule that is then detected on the support. The presence of the reporter molecule on the support indicates the presence of the complex on the support, which in turn indicates the presence of the mutation in the target nucleic acid sequence. An example of a system as described above is the enzyme-linked immunosorbent assay (ELISA), a description of which is found in "Enzyme-Immunoassay," Edward T. Maggio, editor, CRC Press, Inc., Boca Raton, Fla. (1980) wherein, for example, the sbp member is biotin, the complementary sbp member is streptavidin and the reporter molecule is an enzyme such as alkaline phosphatase.

Detection of the signal will depend upon the nature of the signal producing system utilized. If the reporter molecule is an enzyme, additional members of the signal producing system would include enzyme substrates and so forth. The product of the enzyme reaction is preferably a luminescent product, or a fluorescent or non-fluorescent dye, any of which can be detected spectrophotometrically, or a product that can be detected by other spectrometric or electrometric means. If the reporter molecule is a fluorescent molecule, the medium can be irradiated and the fluorescence determined. Where the label is a radioactive group, the medium can be counted to determine the radioactive count.

The association of the labels within the complex may also be determined by using labels that provide a signal only if the labels become part of the complex. This approach is particularly attractive when it is desired to conduct the present invention in a homogeneous manner. Such systems include enzyme channeling immunoassay, fluorescence energy transfer immunoassay, electrochemiluminescence assay, induced luminescence assay, latex agglutination and the like.

In one aspect of the present invention detection of the complex is accomplished by employing at least one suspendable particle as a support, which may be bound directly to a nucleic acid strand or may be bound to an sbp member that is complementary to an sbp member attached to a nucleic acid strand. Such a particle serves as a means of segregating the bound target polynucleotide sequence from the bulk solution, for example, by settling, electrophoretic separation or magnetic separation. A second label, which becomes part of the complex if a mutation is present, is a part of the signal producing system that is separated or concentrated in a small region of the solution to facilitate detection. Typical labels that may be used in this particular embodiment are fluorescent labels, particles containing a sensitizer and a chemiluminescent olefin (see U.S. Ser. No. 07/923,069 filed Jul. 31, 1992, the disclosure of which is incorporated herein by reference), chemiluminescent and electroluminescent labels.

Preferably, the particle itself can serve as part of a signal producing system that can function without separation or segregation. The second label is also part of the signal producing system and can produce a signal in concert with the particle to provide a homogeneous assay detection method. A variety of combinations of labels can be used for this purpose. When all the reagents are added at the beginning of the reaction, the labels are limited to those that are stable to the elevated temperatures used for amplification, chain extension, and branch migration. In that regard it is desirable to employ as labels polynucleotide or polynucleotide analogs having 5 to 20 or more nucleotides depending on the nucleotides used and the nature of the analog. Polynucleotide analogs include structures such as polyribonucleotides, polynucleoside phosphonates, peptidonucleic acids, polynucleoside phosphorothioates, homo DNA and the like. In general, unchanged nucleic acid analogs provide stronger binding and shorter sequences can be used. Included in the reaction medium are oligonucleotide or polynucleotide analogs that have sequences of nucleotides that are complementary. One of these oligonucleotides oligonucleotide analogs is attached to, for example, a reporter molecule or a particle. The other is attached to a primer, either primer P2 or primer P1 and/or P3 as a label. Neither the oligonucieotide nor polynucleotide analog should serve as a polynucleotide polymerase template. This is achieved by using either a polynucleotide analog or a polynucleotide that is connected to the primer by an abasic group. The abasic group comprises a chain of 1 to 20 or more atoms, preferably at least 6 atoms, more preferably, 6 to 12 atoms such as, for example, carbon, hydrogen, nitrogen, oxygen, sulfur, and phosphorus, which may be present as various groups such as polymethylenes, polymethylene ethers, hydroxylated polymethylenes, and so forth. The abasic group conveniently may be introduced into the primer during solid phase synthesis by standard methods.

Under the proper annealing temperature an oligonucleotide or polynucleotide analog attached to a reporter molecule or particle can bind to its complementary polynucleotide analog or oligonucleotide separated by an abasic site that has become incorporated into partial duplexes A' and B' as labels during amplification. If the partial duplexes become part of a quadramolecular complex, the reporter molecule or particle becomes part of the complex. By using different polynucleotide analogs or oligonucleotide sequences for labels, L1 and L2, two different reporter molecules or particles can become part of the complex. Various combinations of particles and reporter molecules can be used.

The particles, for example, may be simple latex particles or may be particles comprising a sensitizer, chemiluminescer, fluorescer, dye, and the like. Typical particle/reporter molecule pairs include a dye crystallite and a fluorescent label where binding causes fluorescence quenching or a tritiated reporter molecule and a particle containing a scintillator. Typical reporter molecule pairs include a fluorescent energy donor and a fluorescent acceptor dye. Typical particle pairs include (1) two latex particles, the association of which is detected by light scattering or turbidimetry, (2) one particle capable of absorbing light and a second label particle which fluoresces upon accepting energy from the first, and (3) one particle incorporating a sensitizer and a second particle incorporating a chemiluminescer as described for the induced luminescence immunoassay referred to in U.S. Ser. No. 07/704,569, filed May 22, 1991, entitled "Assay Method Utilizing Induced Luminescence", which disclosure is incorporated herein by reference.

Briefly, detection of the quadramolecular complex using the induced luminescence assay as applied in the present invention involves employing a photosensitizer as part of one label and a chemiluminescent compound as part of the other label. If the complex is present the photosensitizer and the chemiluminescent compound come into close proximity. The photosensitizer generates singlet oxygen and activates the chemiluminescent compound when the two labels are in close proximity. The activated chemiluminescent compound subsequently produces light. The amount of light produced is related to the amount of the complex formed.

By way of illustration as applied to the present invention, a particle is employed, which comprises the chemiluminescent compound associated therewith such as by incorporation therein or attachment thereto. The particles have a recognition sequence, usually an oligonucleotide or polynucleotide analog, attached thereto with a complementary sequence incorporated into one of the nucleic acid strands as a label, L1. Another particle is employed that has the photosensitizer associated therewith. These particles have a recognition sequence attached thereto, which is different than that attached to the chemiluminescent particles. A complementary sequence is incorporated as a label L2 in the nucleic acid strand in complex C that is not complementary to the nucleic acid strand carrying label L1. Once the medium has been treated in accordance with the present invention to form a quadramolecular complex C, the medium is irradiated with light to excite the photosensitizer, which is capable in its excited state of activating oxygen to a singlet state. Because the chemiluminescent compound of one of the sets of particles is now in close proximity to the photosensitizer by virtue of the presence of the target polynucleotide having a mutation, the chemiluminescent compound is activated by the singlet oxygen and emits luminescence. The medium is then examined for the presence and/or the amount of luminescence or light emitted, the presence thereof being related to the presence of quadramolecular complex C. The presence of the latter indicates the presence and/or amount of the target polynucleotide having a mutation or of the target polynucleotide itself.

Another aspect of the present invention is depicted in FIG. 6. A method is shown for preparing a DNA partial duplex having a portion at an end thereof that has two predefined non-complementary single stranded sequences B1 and B2. A medium containing a double stranded nucleic acid B is combined with a polymerase, nucleoside triphosphates and two primers, P3 and P2. P3 is extendable along one of the strands of the nucleic acid. P3 has a 3'-end portion Pa that does bind to this strand and a 5'-end portion A1 that does not bind thereto. P2 is extendable along the other of the strands of the nucleic acid. Extended primer produced by the extension of one of the primers is a template for the other of the primers. The medium is subjected to temperature cycling to extend the primers. As a result duplex BB is produced. The conditions for carrying out this step are the same as those described above for amplification of a nucleic acid. The medium is then combined with a primer P1, which has 3'-end portion Pa and a 5'-end portion B1 that does not bind to the extended primers of duplex BB. The medium is next subjected to conditions such that P1 binds to and is extended along extended primer P2 to produce only a complement, and not a copy, of the extended primer. The conditions employed are as described above for chain extension of a primer only, not as part of an amplification. A partial duplex B' is formed that contains non-complementary end portions B1 and B2. These end portions are predefined by virtue of the primers employed in the reaction permitting one to introduce desired non-complementary sequences at the end of a double stranded nucleic acid.

Another aspect of the present invention is a method of preparing a DNA partial duplex having a portion at one end that has two non-complementary single stranded sequences. FIG. 7 depicts such a method in accordance with the present invention. A medium containing a single stranded polynucleotide SSP is combined with a primer P1 that has a 3'-end portion Pa, which binds to a sequence that is 8 to 60 nucleotides from the 3'-end of SSP. Primer P1 also has an 8 to 60 nucleotide portion B1 that does not bind to SSP. The medium is subjected to conditions under which P1 binds to and is extended along the single stranded polynucleotide. The complement of SSP is formed but not a copy thereof. The conditions employed are as described above for chain extension of a primer only, not as part of an amplification. A duplex B' is formed and contains non-complementary end portions B1 and B2.

As mentioned above, the present invention also provides for detection of a target sequence using PCR. An example of this embodiment is depicted in FIG. 8. This PCR method involves formation of a four-strand structure or complex as above for the detection of a mutation. However, in the approach in FIG. 8 the target nucleic acid sequence A is the sequence to be detected by PCR and the reference nucleic acid sequence B is introduced as a reagent and contains a difference Q from the target nucleic acid sequence. This difference is as described above for two related nucleic acid sequences. Thus, in this embodiment the identity of the target nucleic acid sequence is known to the extent necessary to allow the preparation of the primers and the reference nucleic acid sequence. The formation of such complex involves producing two partial duplexes by amplification by using three different primers in the polymerase chain reaction and allowing the amplified products to anneal. In this particular embodiment the formation of the complex is dependent on the presence of the target nucleic acid sequence. If the target nucleic acid sequence is not present, no complex is detected. However, when the target nucleic acid is present, there is a difference between the two hybridized portions of the complex. The complex does not dissociate and can be detected as an indication of the presence of the target nucleic acid sequence.

Referring now to FIG. 8, target nucleic acid A, if present, is amplified by the polymerase chain reaction using primers P1 and P2 to produce an amplicon AA. Primer P2 contains a label L1 and primer P1 is comprised of a 3'-end portion Pa that can hybridize with the target sequence and 5'-end portion B1 that cannot hybridize with the target sequence. The amplification is carried out under the reaction conditions employed in PCR in the presence of a nucleotide polymerase and nucleoside triphosphates using temperature cycling. Amplicon AA has two strands, a labeled strand derived from primer P2 and an unlabeled strand derived from primer P1. The unlabeled strand has a 5'-end portion B1 of primer P1 and the labeled strand has a corresponding 3'-end portion A2, which is the complement of B1.

A chain extension of primer P3 along the labeled strand of amplicon AA is then carried out to produce tailed target partial duplex A'. Primer P3 is comprised of a 3'-end portion Pa, which is identical to Pa of primer P1 and which binds to the labeled strand of M. P3 has 5'-end portion A1 that is not complementary to amplicon AA. The chain extension is carried out in the presence of a nucleotide polymerase and nucleoside triphosphates under appropriate temperature conditions so that only the complementary strand of the labeled strand is produced and not a copy. This complementary unlabeled strand of tailed target partial duplex A' has a 5'-end portion A1, which is not complementary to the 3'-end portion A2 of the labeled strand of A'. Unless the PCR reaction is carried out to produce an excess of the labeled strand, there will also be present the unlabeled strand from the amplification. This strand is not a template during chain extension to form partial duplex A'.

In the embodiment of FIG. 8, reference nucleic acid sequence B is in a separate medium, using primer P2 and primer P3, by polymerase chain reaction to produce amplicon BB. The amplification is carried out using temperature cycling under the conditions described above in the presence of a nucleotide polymerase and nucleoside triphosphates. B is comprised of a sequence identical to A except for difference Q. Generally, primer P2 used for this amplification contains a label L2 that may be the same as or different than L1. Amplicon BB has two strands, a labeled strand derived from primer P2 and an unlabeled strand derived from primer P3. The unlabeled strand has end portion A1 of primer P3 and the labeled strand has corresponding end portion B2, which is the complement of A1.

A chain extension of primer P1 along the labeled strand of amplicon BB is carried out, under the conditions mentioned above for the chain extension of primer P3 along the labeled strand in duplex AA, to produce tailed reference partial duplex B'. As mentioned above, primer P1 is comprised of portion Pa, which binds to the labeled strand of BB and portion B1 that does not bind to amplicon BB. The chain extension is carried out in the presence of a nucleotide polymerase and nucleoside triphosphates under appropriate temperature conditions so that only the complement of the labeled strand is produced and not a copy. The extended primer P1 has a 5'-end portion B1, which is not complementary to end portion B2 of the labeled strand of B'. As can be seen, A' and B' are related in that each of their labeled strands is complementary to the unlabeled strand of the other except for difference Q.

The strands of partial duplexes A' and B' are allowed to bind and undergo branch migration by combining the mixtures containing partial duplexes A' and B' and incubating the combination under conditions described above for mutation detection wherein complex C' is formed if the target nucleic acid sequence is present. Oligonucleotide tail A1 of A' is hybridized to corresponding oligonucleotide tail B2 of B' and, similarly, oligonucleotide tail A2 of A' is hybridized to oligonucleotide tail B1 of B'. Branch migration within complex C' continues until difference Q is reached, at which point migration ceases. In the embodiment depicted in FIG. 8, labels L1 and L2 are incorporated into the partial duplexes that comprise complex C'.

In the embodiment of FIG. 8, the reactions are carried out independently to produce tailed partial duplexes A' and B', respectively. Then, the reaction mixtures can be combined to allow the respective strands of A' and B' to bind to one another to form complex C'.

It is a particularly attractive feature of the present invention that the method for the use of PCR in the detection of a target nucleic acid sequence can be carried out in a single reaction container without a separation step. In this embodiment, a combination is provided in a single medium. The combination comprises (i) a sample suspected of containing a target nucleic acid sequence, (ii) a reference nucleic acid sequence, related to but different from the target nucleic acid sequence, (iii) a nucleotide polymerase, (iv) nucleoside triphosphates, and (v) primers P1, P2 and P3, wherein P2 may include primer P2 labeled with L1 and primer P2 labeled with L2, or P2 may be unlabeled and primers P1 and P3 may be labeled respectively with L1 and L2. The medium is then subjected to multiple temperature cycles of heating and cooling to simultaneously achieve all of the amplification and chain extension reactions described above for FIG. 8 except that in this embodiment there is no need to avoid making copies of any of the extended primers. The medium is subjected to conditions for conducting PCR as described above.

When target nucleic acid is present, all possible partial and complete duplexes are formed that can form from 1) single strands that have any combination of reference or target sequences and 5'-ends A2 and B2, and 2) single strands having any combination of reference or mutant sequences and 5'-ends A1 or B1 wherein the strands may further be labeled with either L1 or L2 when L1 and L2 are different. Among the partial duplexes that are formed are the tailed partial duplexes A' and B', which can bind to each other to form complex C', which does not dissociate. A determination of the presence of such a complex is then made to establish the presence of the target nucleic acid sequence. When primers P1 and P3 are labeled instead of primer P2, the labels L1 and L2 in partial duplexes A' and B' are attached to tails A1 and B1, respectively, which still provides for detection of complex C' when target nucleic acid sequence is present.

When target nucleic acid sequence is not present (see FIG. 8A), two duplexes form by virtue of the amplification of the reference nucleic acid sequence wherein one can achieve an initial PCR amplification with both sets of primers, namely, P2 and P3 on the one hand (represented by duplex BB in FIG. 8A) and P2 and P1 on the other (represented by duplex bb in FIG. 8A). Chain extension of primer P1 on amplicon BB produces B', and chain extension primer P3 on amplicon bb produces b'. Any four strand structure formed by hybridization of the respective tails of B' and b' to one another completely dissociates because there is no difference in either of the duplexes to inhibit complete strand exchange. In other words, the complex dissociates into normal duplex structures D' and E' by strand exchange by means of branch migration when the hybridized portions of each partial duplex are identical. In this embodiment in the absence of target nucleic acid sequence, the hybridized portions are identical in that each strand contains difference Q.

As a matter of convenience, predetermined amounts of reagents employed in the present invention can be provided in a kit in packaged combination. A kit can comprise in packaged combination (a) a primer P2 that is extendable along one of the strands of the target and reference nucleic acid sequences, (b) a primer P1 comprising a 3'-end portion Pa that binds to and is extendable along the other of the strands of the target and reference nucleic acid sequences and a 5'-end portion B1 that does not bind to the target and reference nucleic acid sequences, and (c) a primer P3 comprising 3'-end portion Pa and a portion A1 that is different from B1 and does not bind to the target and reference nucleic acid sequences. Preferably, primer P2 can be labeled, but primers P1 and P3 alternatively may be labeled. The kit can also include a reference nucleic acid, which corresponds to a target nucleic acid sequence except for the possible presence of a difference such as a mutation, and reagents for conducting an amplification of target nucleic acid sequence prior to subjecting the target nucleic acid sequence to the methods of the present invention. The kit can also include nucleoside triphosphates and a nucleotide polymerase. The kit can further include two additional oligonucleotide primers PX1 and PX2 where the primers are related in that a product of the extension of one along the target sequence serves as a template for the extension of the other. The kit can further include particles as described above capable of binding to the label on at least one of the primers. The kit can further include members of a signal producing system and also various buffered media, some of which may contain one or more of the above reagents. Preferably, primers PX1, PX2, P1, P2 and P3 are packaged in a single container. More preferably, at least all of the above components other than buffer are packaged in a single container.

The kit can further include a pair of adapter primers for amplifying the target and reference nucleic acids. One of the primers has a 3'-end portion that is hybridizable to the target and reference nucleic acids and a portion 5' thereof that is not hybridizable with the target or reference nucleic acids and is substantially identical to primer P2. The other of the primers has a 3'-end portion that is hybridizable to the target and reference nucleic acids and a portion 5' thereof that is not hybridizable with the target or reference nucleic acids and is substantially identical to the 3'-end portion Pa of primers P1 and P3. The adapter primers are usually packaged in a container separate from primers P1, P2 and P3.

The relative amounts of the various reagents in the kits can be varied widely to provide for concentrations of the reagents which substantially optimize the reactions that need to occur during the present method and to further substantially optimize the sensitivity of the method in detecting a mutation. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. Each reagent can be packaged in separate containers or some or all of the reagents can be combined in one container where cross-reactivity and shelf life permit. In a particular embodiment of a kit in accordance with the present invention, the reagents are packaged in a single container. The kits may also include a written description of a method in accordance with the present invention as described above.

EXAMPLES

The invention is demonstrated further by the following illustrative examples. Temperatures are in degrees centigrade (° C.) and parts and percentages are by weight, unless otherwise indicated. The following definitions and abbreviations are used herein:

Tris—Tris(hydroxymethyl)aminomethane-HCl (a 10×solution) from BioWhittaker, Walkersville, Md.
BSA—bovine serum albumin from Gibco BRL, Gaithersburg Md.
bp—base pairs
wt (+)—wild type allele
mut (−)—mutant allele
+/+—homozygote with 2 normal alleles
−/−—homozygote with 2 mutant alleles
+/−—heterozygote with 1 normal and 1 mutant allele
Target sample—DNA sample to be tested for the presence of a mutation;
Reference sample—DNA sample homozygous for the wt sequence with which target samples are challenged.
sec—seconds
hr—hours
min—minutes
Buffer A—10 mM Tris-HCl (pH 8.3), 50 mM KCl, 4 mM $MgCl_2$, 200 µg/ml BSA
Buffer B—10 mM Tris-HCl (pH 8.3), 50 mM KCl, 20 mM $MgCl_2$, 200 µg/ml BSA
Buffer C—0.1M Tris, 0.3M NaCl, 25 mM EDTA, 0.1% BSA, 0.1% dextran T-500, a 1:320 dilution of mouse IgG (HBR-1 from Scantibodies Laboratory Inc., Los Angeles, Calif.), 0.05% Kathon (Rohm and Haas, Philadelphia, Pa.), and 0.01% gentamycin sulfate.
RLU—relative light units
nt—nucleotides
MAD—maleimidylaminodextran
Ab—antibody
Sav—streptavidin
MOPS—3-(N-morpholino)propane sulfonic acid
hr—hour
sulfo-SMCC—sulfosuccinimidyl 4-(N-maleimidomethyl)cyclohexane-1-carboxylate
NHS—N-hydroxysuccinimide
EDAC—1-ethyl-3-(3-dimethylaminopropyl) carbodiimide hydrochloride
DMSO—dimethylsulfoxide
MES—morpholinoethanesulfonate
rpm—rotations per min
EDTA—ethylenediaminetetraacetic acid
SATA—N-succinimidyl S-acetylthioacetate
BSA—bovine serum albumin from Sigma Chemical Company, St. Louis Mo.
eq—equivalents
bp—base pairs
$A_{280}$—absorbance at wavelength 280 nanometers
DexAl—dextran aldehyde
DPP—4,7-diphenylphenanthroline
$Eu(TTA)_3$—europium tri-3-(2-thienoyl)-1,1,1-trifluoroacetonate
L or l—liter
exo VII—exonuclease VII from *E. coli* (from Amersham Life Science) (USB).
DMF—dimethyl formamide
THF—tetrahydrofuran
MS—mass spectroscopy
NMR—nuclear magnetic resonance spectroscopy
TMSCl—tetramethylsilylchloride
ELISA—enzyme linked immunosorbent assay as described in "Enzyme-Immunoassay," Edward T. Maggio, CRC Press, Inc., Boca Raton, Fla. (1980)

Monoclonal antibodies were produced by standard hybrid cell technology. Briefly, the appropriated immunogen was injected into a host, usually a mouse or other suitable animal, and after a suitable period of time the spleen cells from the host were obtained. Alternatively, unsensitized cells from the host were isolated and directly sensitized with the immunogen in vitro. Hybrid cells were formed by fusing the above cells with an appropriate myeloma cell line and culturing the fused cells. The antibodies produced by the cultured hybrid cells were screened for their binding affinity to the particular antigen, dig-BSA conjugate. A number of screening techniques were employed such as, for example, ELISA screens. Selected fusions were then recloned.

Beads:

Acc-Ab$_{Dig}$—Acceptor beads coupled (MAD) to the anti-Dig antibody (with 377 antibody molecules per bead) were prepared as follows:

Hydroxypropylaminodextran (1NH$_2$/7 glucose) was prepared by dissolving Dextran T-500 (Pharmacia, Uppsala, Sweden) (50 g) in 150 mL of H$_2$O in a 3-neck round-bottom flask equipped with mechanical stirrer and dropping funnel. To the above solution was added 18.8 g of Zn (BF$_4$)$_2$ and the temperature was brought to 87° C. with a hot water bath. Epichlorohydrin (350 mL) was added dropwise with stirring over about 30 min while the temperature was maintained at 87–88° C. The mixture was stirred for 4 hr while the temperature was maintained between 80° C. and 95° C., then the mixture was cooled to room temperature. Chlorodextran product was precipitated by pouring slowly into 3 L of methanol with vigorous stirring, recovered by filtration and dried overnight in a vacuum oven.

The chlorodextran product was dissolved in 200 mL of water and added to 2 L of concentrated aqueous ammonia (36%). This solution was stirred for 4 days at room temperature, then concentrated to about 190 mL on a rotary evaporator. The concentrate was divided into two equal batches, and each batch was precipitated by pouring slowly into 2 L of rapidly stirring methanol. The final product was recovered by filtration and dried under vacuum.

Hydroxypropylaminodextran (1NH$_2$/7 glucose), prepared above, was dissolved in 50 mM MOPS, pH 7.2, at 12.5 mg/mL. The solution was stirred for 8 hr at room temperature, stored under refrigeration and centrifuged for 45 min at 15,000 rpm in a Sorvall RC-5B centrifuge immediately before use to remove a trace of solid material. To 10 mL of this solution was added 23.1 mg of Sulfo-SMCC in 1 mL of water. This mixture was incubated for 1 hr at room temperature and used without further purification.

C-28 thioxene was prepared as follows:

To a solution of 4-bromoaniline (30 g, 174 mmol) in dry DMF (200 mL) was added 1-bromotetradecane (89.3 mL, 366 mmol) and N,N-diisopropylethylamine (62.2 mL, 357 mmol). The reaction solution was heated at 90° C. for 16 hr under argon before being cooled to room temperature. To this reaction solution was again added 1-bromotetradecane (45 mL, 184 mmol) and N,N-diisopropylethylamine (31 mL, 178 mmol) and the reaction mixture was heated at 90° C. for another 15 hr. After cooling, the reaction solution was concentrated in vacuo and the residue was diluted with CH$_2$Cl$_2$ (400 mL). The CH$_2$Cl$_2$ solution was washed with 1 N aqueous NaOH (2×), H$_2$O, and brine, was dried over Na$_2$SO$_4$ and was concentrated in vacuo to yield a dark brown oil (about 110 g). Preparative column chromatography on silica gel by a Waters 500 Prep LC system eluting with hexane afforded a yellow oil that contained mainly the product (4-bromo-N,N-di-(C$_{14}$H$_{29}$)-aniline) along with a minor component 1-bromotetradecane. The latter compound was removed from the mixture by vacuum distillation (bp 105–110° C., 0.6 mm) to leave 50.2 g (51%) of the product as a brown oil. To a mixture of magnesium turnings (9.60 g, 395 mmol) in dry THF (30 mL) under argon was added dropwise a solution of the above substituted aniline product (44.7 g, 79 mmol) in THF (250 mL). A few crystals of iodine were added to initiate the formation of the Grignard reagent. When the reaction mixture became warm and began to reflux, the addition rate was regulated to maintain a gentle reflux. After addition was complete, the mixture was heated at reflux for an additional hour. The cooled supernatant solution was transferred via cannula to an addition funnel and added dropwise (over 2.5 hr) to a solution of phenylglyoxal (11.7 g, 87 mmol) in THF (300 mL) at −30° C. under argon. The reaction mixture was gradually warmed to 0° C. over 1 hr an stirred for another 30 min. The resulting mixture was poured into a mixture of ice water (800 mL) and ethyl acetate (250 mL). The organic phase was separated and the aqueous phase was extracted with ethyl acetate (3×). The combined organic phases were washed with H$_2$O (2×), brine and was dried over MgSO$_4$. Evaporation of the solvent gave 48.8 g of the crude product as a dark green oily liquid. Flash column chromatography of this liquid (gradient elution with hexane, 1.5:98.5, 3:97, 5:95 ethyl acetate:hexane) afforded 24.7 g (50%) of the benzoin product (MS (C$_{42}$H$_{69}$NO$_2$): [M-H]$^+$ 618.6, $^1$H NMR (250 MHz, CDCl$_3$) was consistent with the expected benzoin product. To a solution of the benzoin product from above (24.7 g, 40 mmol) in dry toluene (500 mL) was added sequentially 2-mercaptoethanol (25 g, 320 mmol) and TMSCl (100 mL, 788 mmol). The reaction solution was heated at reflux for 23 hr under argon before being cooled to room temperature. To this was added additional TMSCl (50 mL, 394 mmol); and the reaction solution was heated at reflux for another 3 hr. The resulting solution was cooled, was made basic with cold 2.5N aqueous NaOH and was extracted with CH$_2$Cl$_2$ (3×). The combined organic layers were washed with saturated aqueous NaHCO$_3$ (2×) and brine, was dried over Na$_2$SO$_4$ and was concentrated in vacuo to give a brown oily liquid. Preparative column chromatography on silica gel by using a Waters 500 Prep LC system (gradient elution with hexane, 1:99, 2:98 ethyl acetate:hexane) provided 15.5 g (60%) of the C-28 thioxene as an orange-yellow oil (MS (C$_{44}$H$_{71}$NOS): [M-H]$^+$ 661.6, $^1$H NMR (250 MHz, CDCl$_3$) was consistent with the expected C-28 thioxene product 2-(4-(N,N-di-(C$_{14}$H$_{29}$)-anilino)-3-phenyl thioxene.

Carboxyl acceptor beads were prepared as follows: The starting beads were carboxylate modified latex purchased from Seradyn Particle Technology, Indianapolis, Ind. The beads contained Eu(TTA)$_3$DPP prepared as follows: DPP/Eu(TTA)$_3$ was prepared by combining 8.69 g of Eu(TTA)$_3$.3H$_2$O (10 mmoles, Kodak Chemical Company, Rochester N.Y.) and 1.8 g of 1,10-phenanthroline (10 mmoles, Aldrich) in 50 ml of dry toluene and heating to 95° C. in an oil bath for one 1 hour. Toluene was removed under reduced pressure. The ash colored solid was crystallized from 10 ml of toluene to yield 10 grams of DPP/Eu(TTA)$_3$. Absorption spectrum: 270 nm (20,000), 340 nm (60,000) (Toluene) 1.R(KBr): Cm$^{-1}$: 3440(s), 1600(s), 1540(s), 1400(s), 1300 (s). Four mL of 20% suspension (400 mg) of washed 175 nm carboxylate modified latex was diluted with 3 mL of ethoxyethanol in a 25 mL round bottom (R.B.) flask with a stir bar. The R.B. flask was then placed in an oil bath at 105° C. and stirred for 10 minutes. Then, 3.3 mM C-28 thioxene and 15.5 mM Eu(TTA)$_3$DPP was added; the beads were stirred for 5 minutes more. At this point 1.0 mL of 0.1 N NaOH was added slowly over 5 minutes. During all the additions, the oil bath temperature was maintained at 105° C. The oil bath temperature was slowly allowed to drop to room temperature over 2 hours. After cooling, the mixture was diluted with 20 mL of ethanol and centrifuged (12,500 rpm, 30 minutes). Supernatants were discarded and the pellets resuspended in ethanol by sonication. Centrifugation was repeated, and the pellet was resuspended in water; and centrifugation was repeated. The pellet was resuspended in 5 mL of aqueous ethanol to a final volume of 40 mL.

Carboxyl acceptor beads prepared above (99 mg in 4.5 mL water) were added slowly with vortexing to 5.5 mL of MAD aminodextran from above, followed by 1 mL of 200 mg/mL NHS in 50 mM MES, pH 6,1 mL of 200 mg/mL EDAC in water, and 450 µL of 1 M HCl, final pH 6. The mixture was incubated overnight at room temperature in the dark, then reacted with 200 mg succinic anhydride in 0.5 mL of DMSO for 30 min at room temperature. Freshly opened Surfact-Amps Tween-20 (Pierce Chemical Company, Rockford, Ill.) was added and the beads were centrifuged 30 min at 15,000 rpm in a Sorvall RC-5B centrifuge, washed by centrifugation with three 10 mL portions of 50 mM MOPS, 50 mM EDTA, 0.1% Surfact-Amps Tween-20 (Pierce Chemical Company), pH 7.2, and resuspended in 3 mL of the same.

Monoclonal anti-digoxin Ab (prepared as described above) was purified by ABx resin (Baker Chemical Company, Phillipsburg, N.J.) and was dialyzed into 0.15 M NaCl, 5 mM $Na_2HPO_4$, pH 7.4. The anti-digoxin Ab was thiolated by mixing 622 µL (4.28 mg) with 10.2 AL of SATA (1.25 mg/mL in ethanol, 2 eq.), incubating for 1 hr at room temperature and dialyzing cold against 2×2 L of 150 mM NaCl, 10 mM $Na_2HPO_4$, 1 mM EDTA, pH7. The thioacetylated antibody was deacetylated by adding 62.2 µL of hydroxylamine (1 M $H_2NOH$, 50 mM MOPS, 25 mM EDTA, pH 7), bubbling with argon and incubating for 1 hr at room temperature. The product was applied to a Pharmacia PD-10 column (G-25) and eluted with 50 mM MOPS, 50 mM EDTA, pH 7.2, bubbled with argon. After 2.5 mL fore-run, three-1 mL fractions were collected and combined. Recovery of antibody was 3.66 mg or 86% by $A_{280}$. Surfact-Amps Tween-20 (10%) was added to give 0.2% final concentration.

A 1.4 mL aliquot of the thiolated antibody above (1.71 mg antibody) was immediately added to 300 µL (10 mg) of maleimidated beads prepared above plus enough 10% Tween-20 to bring final concentration of the mixture to 0.2%. The tube was purged with argon and incubated overnight at room temperature in the dark. To the above was added 3.4 µL of 1 M $HSCH_2COOH$ in water. After 30 min at room temperature, 6.8 µL of $ICH_2COOH$ (1 M in water) was added. After 30 min 3.5 mL of 0.17M glycine, 0.1 M NaCl, 0.1% (v/v) Tween-20, 10 mg/mL BSA, pH 9.2 was added and the beads were centrifuged (30 min at 15,000 rpm), incubated for 3 hr in 5 mL of the same buffer, centrifuged, washed by centrifugation with three-5 mL portions of Buffer C, resuspended in 5 mL of Buffer C and stored under refrigeration. The size of the beads, determined in Buffer C, was 301+/−56 nm. Binding capacity was determined with 125I-digoxin and was equivalent to 377 antibody molecules per bead.

Silicon tetra-t-butyl phthalocyanine was prepared as follows: Sodium metal, freshly cut (5.0 g, 208 mmol), was added to 300 mL of anhydrous ether in a two-liter, 3-necked flask equipped with a magnetic stirrer, reflux condenser, a drying tube and a gas bubbler. After the sodium was completely dissolved, 4-t-butyl-1,2-dicyanobenzene (38.64 g, 210 mmol, from TCI Chemicals, Portland Oreg.) was added using a funnel. The mixture became clear and the temperature increased to about 50° C. At this point a continuous stream of anhydrous ammonia gas was introduced through the glass bubbler into the reaction mixture for 1 hr. The reaction mixture was then heated under reflux for 4 hr. while the stream of ammonia gas continued. During the course of the reaction, as solid started to precipitate. The resulting suspension was evaporated to dryness (house vacuum) and the residue was suspended in water (400 mL) and filtered. The solid was dried (60° C., house vacuum, $P_2O_5$). The yield of the product (1,3-diiminoisoindoline, 42.2 g) was almost quantitative. This material was used for the next step without further purification. To a one-liter, three-necked flask equipped with a condenser and a drying tube was added the above product (18 g, 89 mmol) and quinoline (200 mL, Aldrich Chemical Company, St. Louis Mo.). Silicon tetrachloride (11 mL, 95 mmol, Aldrich Chemical Company) was added with a syringe to the stirred solution over a period of 10 minutes. After the addition was completed, the reaction mixture was heated to 180–185° C. in an oil bath for 1 hr. The reaction was allowed to cool to room temperature and concentrated HCl was carefully added to acidify the reaction mixture (pH 5–6). The dark brown reaction mixture was cooled and filtered. The solid was washed with 100 mL of water and dried (house vacuum, 60° C., $P_2O_5$). The solid material was placed in a 1-liter, round bottom flask an concentrated sulfuric acid (500 mL) was added with stirring. The mixture was stirred for 4 hr. at 60° C. and was then carefully diluted with crushed ice (2000 g). The resulting mixture was filtered and the solid wad washed with 100 mL of water and dried. The dark blue solid was transferred to a 1-liter, round bottom flask, concentrated ammonia (500 mL) was added, and the mixture was heated and stirred under reflux for 2 hr., was cooled to room temperature and was filtered. The solid was washed with 50 mL of water and dried under vacuum (house vacuum, 60° C., $P_2O_5$) to give 12 g of product silicon tetra-t-butyl phthalocyanine as a dark blue solid. 3-picoline (12 g, from Aldrich Chemical Company), tri-n-butyl amine (anhydrous, 40 mL) and tri-n-hexyl chlorosilane (11.5 g) were added to 12 g of the above product in a one-liter, three-necked flask, equipped with a magnetic stirrer an a reflux condenser. The mixture was heated under reflux for 1.5 hr. an then cooled to room temperature. The picoline was distilled off under high vacuum (oil pump at about 1 mm Hg) to dryness. The residue was dissolved in $CH_2Cl_2$ and purified using a silica gel column (hexane) to give 10 g of pure product di-(tri-n-hexylsilyl)-silicon tetra-t-butyl phthalocyanine as a dark blue solid. (MS: $[M-H]^+$ 1364.2, absorption spectra: methanol: 674 nm ($\epsilon$ 180,000): toluene 678 nm, $^1H$ NMR (250 MHz, $CDCl_3$): δ: −2.4(m, 12H), −1.3(m, 12H), 0.2–0.9 (m, 54H), 1.8(s, 36H), 8.3(d, 4H) and 9.6 (m, 8H) was consistent with the above expected product.

Sens-Sav—Sensitizer beads coupled to Streptavidin (2300 Sav/bead). The sensitizer beads were prepared placing 600 mL of carboxylate modified beads (Seradyn) in a three-necked, round-bottom flask equipped with a mechanical stirrer, a glass stopper with a thermometer attached to it in one neck, and a funnel in the opposite neck. The flask had been immersed in an oil bath maintained at 94+/−1° C. The beads were added to the flask through the funnel in the neck and the bead container was rinsed with 830 mL of ethoxyethanol, 1700 mL of ethylene glycol and 60 mL of 0.1N NaOH and the rinse was added to the flask through the funnel. The funnel was replaced with a 24–40 rubber septum. The beads were stirred at 765 rpm at a temperature of 94+/−1° C. for 40 min.

Silicon tetra-t-butyl phthalocyanine (10.0 g) was dissolved in 300 mL of benzyl alcohol at 60+/−5° C. and 85 mL was added to the above round bottom flask through the septum by means of a syringe heated to 120+/−10° C. at a rate of 3 mL per min. The remaining 85 mL of the phthalocyanine solution was then added as described above. The syringe and flask originally containing the phthalocyanine was rinsed with 40 mL of benzyl alcohol and transferred to round-bottom flask. After 15 min 900 mL of deionized water and 75 mL of 0.1N NaOH was added dropwise over 40 min. The temperature of the oil bath was allowed to drop slowly to 40+/−10° C. and stirring was then discontinued. The beads were then filtered through a 43 micron polyester filter and subjected to a Microgon tangential flow filtration apparatus (Microgon Inc., Laguna Hills, Calif.) using ethanol:water, 100:0 to 10:90, and then filtered through a 43 micron polyester filter.

Sulfo-SMCC (11.55 mg) was dissolved in 0.5 mL distilled water. Slowly, during 10 sec, the above solution was added to 5 mL of stirring aminodextran (Molecular Probes, Eugene, Oreg.) solution (12.5 mg/mL in 50 mM MOPS, pH 7.2). The mixture was incubated for 1 hr at room temperature.

To the stirring solution above was added 5 mL of 20 mg/mL (100 mg) of the sensitizer beads prepared above in distilled water. Then, 1 mL of 200 mg/mL NHS (prepared fresh in 50 mM MES, pH adjusted to 6.0 with 6N NaOH). 200 mg EDAC was dissolved in 1 mL distilled water and this solution was added slowly with stirring to the sensitizer beads. The pH was adjusted to 6.0 by addition of 450 µL of 1N HCl and the mixture was incubated overnight in the dark. A solution of 100 mg of succinic anhydride in 0.5 mL of DMSO was added to the sensitizer beads and the mixture was incubated for 30 min at room temperature in the dark. To this mixture was added 0.13 mL 10% Tween-20 bringing the final concentration of Tween-20 to 0.1%. The beads were centrifuged for 45 min at 15,000 rpm as above. The supernatant was discarded and the beads were resuspended in 10 mL of buffer (50 mM MOPS, 50 mM EDTA and 0.1% Tween-20, pH 7.2). The mixture was sonicated to disperse the beads. The beads were centrifuged for 30 min as described above, the supernatant was discarded and the beads were resuspended. This procedure was repeated for a total of three times. Then, the beads were resuspended to 40 mg/mL in 2.5 mL of the above buffer, saturated with argon and Tween-20 was added to a concentration of 0.1%. The beads were stored at 4° C.

Streptavidin was bound to the above beads using 25 mg streptavidin for 100 mg of beads. 25 mg streptavidin (50 mg Aaston solid from Aaston, Wellesley, Mass.) was dissolved in 1 mL of 1 mM EDTA, pH 7.5, and 77 µL of 2.5 mg/mL SATA in ethanol was added thereto. The mixture was incubated for 30 min at room temperature. A deacetylation solution was prepared containing 1M hydroxylamine-HCl, 50 mM $Na_2PO_4$, 25 mM EDTA, pH 7.0. 0.1 mL of this deacetylation solution was added to the above solution and incubated for 1 hr at room temperature. The resulting thiolated streptavidin was purified on a Pharmacia PD10 column and washed with a column buffer containing 50 mM MOPS, 50 mM EDTA, pH 7.2. The volume of the sample was brought to 2.5 mL by adding 1.5 mL of the above column buffer. The sample was loaded on the column and eluted with 3.5 mL of the column buffer. The thiolated streptavidin was diluted to 5 mL by adding 1.5 mL of 50 mM MOPS, 50 mM EDTA, 0.1% Tween-20, pH 7.2. 5 mL of the thiolated streptavidin solution was added to 5 mL of the sensitizer beads, under argon, and mixed well. The beads were topped with argon for 1 min, the tube was sealed and the reaction mixture was incubated overnight at room temperature in the dark.

To the above beads was added 7.5 mL of 50 mM MOPS, 50 mM EDTA, 0.1% Tween-20, pH 7.2 to bring the beads to 1 mg/mL. The remaining maleimides were capped by adding mercaptoacetic acid at a final concentration of 2 mM. The mixture was incubated in the dark for 30 min at room temperature. The remaining thiols were capped by adding iodoacetic acid at a final concentration of 10 mM and the mixture was incubated at room temperature for 30 min in the dark. The beads were centrifuged for 30 min at 15,000 rpm as above for a total of three times.

Example 1

Detection of Difference in Nucleic Acid Using Step-Wise Approach

Genomic DNA having the following point mutations within exon 11 of the CFTR gene used herein:

Heterozygous DNA with one wild type (wt) allele and one of the following mutant alleles:

G542X (G>T substitution) from Roche Molecular Systems, Alameda, Calif.;

G551 D (G>A substitution) from Roche Molecular Systems, Alameda, Calif.;

R553X (C>T substitution) from Roche Molecular Systems, Alameda, Calif.;

R560T (G>C substitution) from Roche Molecular Systems, Alameda, Calif.

Homozygous DNA:

G542X/G542X from Coriell Institute for Medical Research, Camden, N.J.

Primers:

PX2—forward PCR primer outside the sequence to be tested; 5' CAACTGTGGTTAAAGCAATAGTGT-GATATATGA 3' (SEQ ID NO: 1) from Oligos Etc., Inc., Wilsonville, Oreg.

PX1—reverse PCR primer outside the sequence to be tested; 5'GCACAGATTCTGAGTAACCATAATCTC-TACCA3' (SEQ ID NO: 2) from Oligos Etc., Inc., Wilsonville, Oreg.

P2—forward PCR primer; 5'GCCTTTCAAATTCAGAT-TGAGC 3' (SEQ ID NO: 3) from Oligos Etc., Inc., Wilsonville, Oreg.

P2B—P2 biotinylated at the 5'-end from Genosys Biotechnologies, Inc., The Woodlands, Tex.;

P2D—P2 Dig-labeled at the 5'-end from Genosys Biotechnologies, Inc., The Woodlands, Tex.;

Pa—reverse PCR primer; 5'GACATTTACAGCAAAT-GCTTGC3' (SEQ ID NO: 4) from Oligos Etc., Inc., Wilsonville, Oreg.

P1—reverse PCR primer which has a 3' end that is identical with Pa, but which has a different 5'-"tail" B1 (20 nucleotides long). The "tails" are arbitrary sequences that are not complementary to the genomic sequence; 5'ACCAT-GCTCGAGATTACGAGGACATTTACAG-CAAATGCTTGC3' (SEQ ID NO: 5) from Genosys Biotechnologies, Inc., The Woodlands, Tex.

P3—reverse PCR primer which has a 3' end that is identical with Pa but which has a different 5'-"tail" A1 (20 nucleotides long). The "tails" are arbitrary sequences that are not complementary to the genomic sequence; 5'GATC-CTAGGCCTCACGTATTGACATTTACAG-CAAATGCTTGC3' (SEQ ID NO: 6) from Genosys Biotechnologies, Inc., The Woodlands, Tex.

Step 1 (1st-round PCR).

Two samples containing 10–100 ng genomic DNA from human peripheral blood, one a target sample and the other a reference sample (wild type sample) were amplified using the P2/Pa pair of primers encompassing the hot spot mutation site in exon 11 of the CFTR (cystic fibrosis) gene. A total of 30 cycles in the Ericomp® thermocycler (from Ericomp, San Diego, Calif.) were performed consisting of a 30-sec denaturation step at 94° C., a 1-min reannealing step at 64° C. and a 1-min extension step at 72° C., preceded by a 2-min denaturation of genomic DNA at 95° C. and followed by a 4-min final extension at 72° C. The reaction volume was 100 Fl and the buffer was Buffer A. The concentration of each primer was 250 nM (as below, in steps 2 and 4). A proof-reading thermostable polymerase (Pfu® DNA polymerase, Stratagene Cloning Systems, La Jolla, Calif.) was used. A hot-start technique using TM HotStart 100™ reaction tubes (Molecular Bio-Products, Inc., San Diego, Calif.) was utilized. The resulting PCR product was 203 bp in length.

Step 2 (2nd-round PCR).

The reaction mixtures from above were diluted 1:1000, and 2 µl of these dilutions were used in 100 µl reactions with the primers P2B and P1 for the target sample and P2D and P3 for the reference sample. 20 amplification cycles were run under the same conditions as in Step 1.

Step 3 (Removal of Primers).

0.5 µl (5 U) of exo VII was added to each reaction mixture. Exo VII is a strictly single-strand specific enzyme, with both 5' to 3' and 3' to 5' exonuclease activities. The digestion of the free primers was carried out for 30 min at 37° C., followed by the inactivation of the enzyme (10 min at 95° C.), as described by Li, et al., (1991) Nucleic Acids Research 19, 3139–3141: Eliminating Primers from Completed Polymerase Chain Reactions with Exonuclease VII.

Step 4 (Addition of Tails).

Primers P3 (for the test sample) and P1 (for the reference sample) were added to the reaction mixtures, and the mixtures were subjected to one PCR cycle (30 sec at 94° C., 1 min at 64° C. and 1 min at 72° C.). Usually fresh Pfu DNA polymerase was also added, but this was not obligatory. Inclusion of primer P2 in this step is optional.

Step 5 (Branch Migration).

2 µl of each of the reaction mixtures was combined and 8 µl of buffer A containing 28 mM MgCl$_2$ was added (final concentration 20 mM MgCl$_2$). The reaction mixture was overlaid with 5 µl mineral oil and incubated 30 min at 65° C. Other MgCl$_2$ concentrations (4 mM and 10 mM) were also tested and found to support branch migration. The reaction was also repeated at other incubation temperatures (50, 60 and 70° C.).

Step 6 (Detection).

Acc-Ab$_{Dig}$ and Sens-Sav beads were titrated with varying amounts of the branch migration reaction mixtures with varying ratios of test sample to reference sample to assure a linear response. Amounts of the components were as follows.

A 2 µl aliquot of the branch migration reaction mixture was combined with 100 µl Buffer B containing 5 µl (10 µg) Sens-Sav and 5 µl (10 µg) Acc-Ab$_{Dig}$ beads and incubated for 5 min at 37° C. The reaction mixture was then irradiated with a 150 watt Xenon lamp for 3 sec (3 cycles of 1 sec illumination and 1 sec waiting time) and the signal was then read.

The results of a typical experiment conducted according to the protocol of this Example 1 were as follows (Table 1):

TABLE 1

| Sample | Signal (RLU) |
|---|---|
| Blank | 5368 |
| WT homozygote (+/+) | 14556 |
| G542X/G542X homozygote (−/−) | 739004 |
| G542X/WT heterozygote (+/−) | 343206 |

Example 2

Detection of Difference in Nucleic Acid Using Simplified Step-Wise Approach

Step 1 (1st-round PCR)

Carried out in the same manner as that for Step 1 of Example 1.

Step 2 (2nd-round PCR).

The reaction mixtures from Step 1 were diluted 1:1000, and 2 µl of these dilutions were added to 100 µl reaction mixtures containing primers P2B, P1 and P3 for the test sample and P2D, P1 and P3 for the reference sample. The concentrations of P1 and P3 were 125 nM each. 20 amplification cycles were run under the same conditions as in Step 1.

Step 3 (Branch Migration).

Note that in contrast to Example 1, removal of the primers was not carried out.

The reaction mixtures were combined as in Step 5 of Example 1. The reaction mixture was heated for 1 min. at 95° C. (denaturation) followed by 30 min. at 65° C. During this incubation period the DNA strands were allowed to reanneal in all possible combinations. 50% of double-stranded molecules resulting from reannealing were full length duplexes and another 50% of the double stranded molecules were partial tailed duplexes. Also during the above incubation, these latter molecules interacted with each other forming 4-stranded complexes and undergoing branch migration. Among them, only 2 out of 16 possible combinations (formed by 1 wild type and 1 mutant homoduplex labeled with biotin and digoxin, respectively) were informative and generated signal. The remaining 14 combinations were formed by either 2 homoduplexes of the same kind (both wild type or both mutant) or 2 heteroduplexes. None of these combinations generated signal because they all undergo complete strand exchange.

Step 4 (Detection)

Carried out in the same manner as that for Step 6 of Example 1.

The results of a typical experiment conducted according to Example 2 were as follows (Table 2):

TABLE 2

| Sample | Signal (RLU) |
|---|---|
| blank | 7706 |
| WT homozygote (+/+) | 15748 |
| G542X/G542X homozygote (−/−) | 730744 |
| G542X/WT heterozygote (+/−) | 233728 |

A panel of 10 samples was screened for mutations in exon 11 of the cystic fibrosis gene according to the protocol of this Example 2. All 5 mutants (1 homozygote and 4 heterozygotes) were correctly detected, as shown in the following table (Table 3). Sample WT1 was used as the reference sample.

TABLE 3

| Sample | Signal (RLU) |
|---|---|
| blank | 6016 |
| WT1 (+/+) | 17286 |
| WT2 (+/+) | 17824 |
| WT3 (+/+) | 19318 |
| WT4 (+/+) | 18008 |
| WT5 (+/+) | 17446 |
| G542X/G542X homozygote (−/−) | 840476 |

TABLE 3-continued

| Sample | Signal (RLU) |
|---|---|
| G542X/WT heterozygote (+/−) | 297120 |
| G551D/WT heterozygote (+/−) | 379426 |
| R553X/WT heterozygote (+/−) | 490572 |
| R560T/WT heterozygote (+/−) | 342778 |

The differences in signals obtained for the different mutations reflect slight variations in the amounts of amplicons and not any bias of the method towards particular mutations (in another similar experiment the signals corresponding to these four heterozygotes were also slightly different from each other, but the order was not the same).

Example 3

Detection of Difference in Nucleic Acid Using Partial Step-wise Approach

The protocol followed in Example 2 was simplified further. All reactions, with the exception of the detection step, were carried out in a single reaction container. Steps 1 and 2 were combined as step 2 in this Example 3 so that genomic DNA was used directly as target for the generation of the tailed labeled duplexes. In order to reduce non-specific priming of primers P2B, P2D, P1 and P3, a preliminary amplification of the genomic target was conducted prior to step 2 by also including primers PX2 and PX1. These primers had higher melting temperatures (Tm) than P2B and P2D and P1 and P3, respectively, and each bound upstream of the respective P2B and P2D and P1 and P3 binding sites. This procedure is well known (Erlich, et al., *Science* (1991) 252:1643–1651) and the primers that become active only in step 2 below are known as "nested" or "inner" primers.

The preliminary amplification was carried out by using an annealing temperature that permitted PX1 and PX2 to bind but was above the melting temperatures of the other primers. In this procedure this initial PCR amplification was carried out with thermal cycling (25 cycles) at 94° and 70° C. for periods of 30 sec and 2 min, respectively. The amplification occurring in steps 1 and 2 above (Examples 1 and 2) with primers P2B (test samples), P2D (reference samples), P1 and P3 was carried out by continuing thermal cycling with an annealing temperature that permitted these primers to bind. This second PCR, step 2, was carried out with thermal cycling (12 cycles) at 94°, 64°, and 72° C., for periods of 30 sec, 1 min and 1 min, respectively. The test and the reference samples were mixed and processed as in step 3 of Example 2 (denaturation at 94° C. for 1 min and annealing at 65° C. for 30 minutes). The association of biotin and digoxin was detected by using the signal producing system as in Example 1.

The results are summarized as follows (Table 4):

TABLE 4

| Sample | Signal (RLU) |
|---|---|
| blank | 4846 |
| WT homozygote (+/+) | 12058 |
| G542X/G542X homozygote (−/−) | 200808 |
| G542X/WT heterozygote (+/−) | 99752 |

Example 4

Detection of Difference in Nucleic Acid Using Simultaneous Approach

The protocol followed in Example 3 was further simplified by combining the two amplification reactions and carrying out the amplification reactions simultaneously. Thus, the reaction mixture formed contained the test DNA genomic sample and the reference (wild type) genomic DNA and all the primers, PX1, PX2, P2B, P2D, P1, and P3. This simplified protocol permitted the distinction between mutant or wild type DNA. In this procedure the initial PCR, step 1, and the second PCR, step 2, were carried out with thermal cycling as described in Example 3, above. As in Example 3, branch migration was accomplished by a final denaturation at 94° C. for 1 min and annealing at 65° C. for 30 minutes. The association of biotin and digoxin was detected by using the signal producing system as in Example 1. Typical results from the assay carried out by this protocol, where 20 ng of test and 20 ng of reference genomic DNA per 50 µl reaction were co-amplified in the same tube, were as follows (Table 5):

TABLE 5

| Sample | Signal (RLU) |
|---|---|
| blank | 8046 |
| WT homozygote (+/+) | 12264 |
| G542X/G542X homozygote (−/−) | 167770 |
| G542X/WT heterozygote (+/−) | 102920 |

Note that all the steps in this protocol, except the detection step, were carried out in a single tube.

Example 5

In this example two commercially available thermostable polymerases, Pfu DNA polymerase (Stratagene, La Jolla Calif.) and Taq DNA polymerase (Perkin Elmer, Norwalk Conn.) were utilized. The fidelity of Pfu polymerase (defined as the number of errors per nucleotide per PCR cycle) is known to be 12 times greater than the fidelity of Taq polymerase due to the absence of 3'-5' proofreading exonuclease activity in the latter enzyme (Lundberg, et al. (1991) *Gene* 108:1–6).

The simplified step-wise protocol utilized in Example 2 above was followed with the exception that no wild type probe was necessary since the interest here was in detecting the heterozygotes with one wild type and one mutant allele.

In the 1st PCR, step 1, of the protocol genomic DNAs (40 ng per 50 µL reaction volume) were amplified with the following primers for the purpose of preparing amplicons for this example:

Primer PX2': 5'-CAACTGTGGTTAAAGCAATAGTGT-3' (SEQ ID NO: 7)
Primer PX1': 5'-GCACAGATTCTGAGTAACCATAAT-3' (SEQ ID NO: 8)

Both primers were from Oligos Etc., Inc., Wilsonville, Oreg. The amplifications were carried out in a 96-well block of a UNO thermocycler from Biometra, Tampa Fla.

After the initial denaturation step (95° C. for 4 min), 35 cycles were performed consisting of 94° C. for 30 sec, 58° C. for 1 min and 72° C. for 1 min.

The resulting 425 bp amplicons were diluted 1:1000, and 1 µl (per 50 µl reaction volume) aliquots of these dilutions were amplified in the 2nd PCR, step 2 (20 cycles under the same conditions as in step 1) using the mixture of primers P2B, P2D, P1 and P3 identified above. 0.5 units of either Pfu DNA polymerase or Taq DNA polymerase per 50 µl were used in both step 1 and step 2.

In Step 3 (branch migration), the samples were heated at 95° C. for 1 min. (denaturation) followed by 30 min. at 65° C. Step 4 (detection) was performed exactly as described in Example 1 above.

The results are summarized in Table 6 below:

TABLE 6

| Sample | Pfu | | Taq | |
|---|---|---|---|---|
| | Signal (RLU) | Discrimination factor* | Signal (RLU) | Discrimination factor* |
| blank | 8606 | | 21772 | |
| WT1 (+/+) | 25014 | 1.00 | 125680 | 1.00 |
| WT2 (+/+) | 24968 | 1.00 | 127468 | 1.02 |
| WT3 (+/+) | 28544 | 1.22 | 106574 | 0.83 |
| WT4 (+/+) | 25982 | 1.06 | 125524 | 1.00 |
| WT5 (+/+) | 25206 | 1.01 | 119428 | 0.94 |
| G542X/G542X (−/−) | 24996 | 1.00 | 245542 | 2.15 |
| G542X/WT (+/−) | 1151520 | 69.66 | 889890 | 8.35 |
| G551D/WT (+/−) | 1124920 | 68.03 | 1007210 | 9.48 |
| G553X/WT (+/−) | 1353640 | 81.97 | 1014520 | 9.55 |
| G560T/WT (+/−) | 1249860 | 75.65 | 1132780 | 10.69 |

*Discrimination factor is defined as a ratio of the signal to the WT1 signal after subtraction of signal for the appropriate blanks.

The results in Table 6 show that a thermostable polymerase having a 3'-5' proofreading exonuclease activity is preferred in the present method for preparing amplicons for the purpose of mutation detection using the branch migration assay conducted according to the above protocol.

Example 6

This example describes using ELISA as an alternative method for detection of the branch migration products.

The samples used were as in Example 2 (Table 3) above: wt1, 542X heterozygote and 542X/542X homozygote.

The wells of streptavidin-coated microtiter plates (Reacti-Bind™, Pierce, Rockford, Ill.) were washed once with 300 μl 0.5% DPBS (Dulbecco's Phosphate Buffered Saline; 10×DPBS contains 2 mg/l KCl, 2 mg/l $KH_2PO_4$, 80 mg/l NaCl and 21.6 mg/l $Na_2HPO_4$, 7 $H_2O$), 0.05% Tween 20.

The DNA samples (2 μl) after step 3 (Example 2) were added to the wells containing 300 μl 1×PBS (Phosphate Buffered Saline; 10×PBS contains 1.44 mg/l $KH_2PO_4$, 90 mg/l NaCl and 7.95 mg/l $Na_2HPO_4$), 300 mM NaCl, 0.1% Tween 20, 25% Fetal Calf Serum, 3% BSA, 50 μg/ml sonicated denatured calf thymus DNA. After incubation at 37° C. for 1 hr, the wells were washed 4 times with 300 μl 0.5% DPBS-0.05% Tween 20. 100 μl of 1:1000 dilution of the anti-digoxygenin Fab fragment (horseradish peroxidase conjugate, catalog # 1207733, Boehringer Mannheim, Indianapolis, Ind.) in the same buffer was added and the plate was incubated at 37° C. for 1 hr. The wells were washed 4 times with 300 III 0.5% DPBS-0.05% Tween 20. 100 μl of a 1:1 mixture of the TMB (tetramethylbenzidine) peroxidase substrate and $H_2O_2$ (Kirkegaard & Perry Laboratories, Gaithersburg, Md., product codes 50-76-01 and 50-65-00, respectively) was added and the plate was incubated at room temperature for 30 min. The color development was stopped by adding 100 μl 1 M phosphoric acid and the signals were read using the Titertek Multiscan Plus microplate reader (ICN Biomedicals, Huntsville Ala.).

The results are summarized in Table 7 below:

TABLE 7

| Sample | OD at 450 nm |
|---|---|
| Blank | 0.065 |
| WT homozygote (+/+) | 0.134 |
| G542X/G542X homozygote (−/−) | 2.067 |
| G542X/WT heterozygote (+/−) | 1.036 |

Example 7

The protocol followed for this example was the simplified step-wise protocol described in Example 2 above. In this example a 3-bp deletion, ΔF508, in exon 10 (the most frequently occurring mutation) of the human cystic fibrosis gene (CFTR) was studied.

In the 1st PCR, step 1, human genomic DNA samples (50 ng) (from Roche Molecular Systems, Alameda Calif., except for ΔF508/ΔF508 homozygote(−/−), which was from Coriell Institute for Medical Research, Camden N.J.) were amplified with the following primers:

Primer PX2": 5'-CAAGTGAATCCTGAGCGTGA-3' (SEQ ID NO: 9) and

Primer PX1": 5'-CTAACCGATTGAATATGGAGCC-3' (SEQ ID NO: 10).

Both primers were from Oligos Etc., Inc., Wilsonville, Oreg. The amplification was carried out in a 96-well block of a UNO thermocycler from Biometra, Tampa Fla. to generate a PCR product 340-bp in length. After the initial denaturation step (95° C. for 4 min), 35 cycles were performed consisting of 94° C. for 30 sec, 64° C. for 1 min and 72° C. for 1 min.

The resulting amplicons were diluted 1:1000, and 1 μl (per 50 μl reaction volume) aliquots of these dilutions were amplified in the 2nd PCR, step 2 (20 cycles under the same conditions as in step 1) using a mixture of primers P2'B (or P2'D), P1' and P3'. The resulting PCR products are 220-bp in length.

P2': 5'-CTCAGTTTTCCTGGATTATGCC-3' (SEQ ID NO: 11)

P2'D: digoxygenin-labeled P2' from Genosys Biotechnologies, Inc., Woodlands, Tex.

P2'B: biotinylated P2' from Oligos Etc., Inc., Wilsonville, Oreg.

P1':
5'-ACCATGCTCGAGATTACGAGCTAACCGATTGA
ATATGGAGCC-3' (SEQ ID NO: 12) from Oligos Etc., Inc., Wilsonville, Oreg.

P3': 5'-GATCCTAGGCCTCACGTATTCTAACCGATTGA
ATATGGAGCC-3', (SEQ ID NO: 13) from Oligos Etc., Inc., Wilsonville, Oreg.

Pa as part of primers P1' and P3' is identical to PX1".

WT1 below was used as the reference sample and amplified with primers P2'D, P1' and P3'.

All the test samples were amplified with primers P2'B', P1' and P3'.

In step 3, branch migration, equal volumes of test and reference amplicons were mixed and overlayed with mineral oil. The reaction mixture was heated for 1 min at 95° C. (denaturation) followed by 30 min at 65° C.

Step 4, detection, was carried out exactly as in Example 1. The results are summarized in the Table 8.

TABLE 8

| Sample | Signal (RLU) |
| --- | --- |
| Blank | 4790 |
| WT1 (+/+) | 19834 |
| WT2 (+/+) | 18530 |
| WT3 (+/+) | 19496 |
| WT4 (+/+) | 19972 |
| WT5 (+/+) | 18460 |
| WT6 (+/+) | 19380 |
| WT7 (+/+) | 17980 |
| ΔF508/ΔF508 homozygote (−/−) | 1341990 |
| WT/ΔF508 heterozygote 1 (+/−) | 524236 |
| WT/ΔF508 heterozygote 2 (+/−) | 625440 |

Example 8

Simplified Direct Protocol

In this example the labeled and tailed amplicons for branch migration were prepared directly from genomic DNA without a preliminary amplification step. Accordingly, this example does not include the 1st PCR step (step 1 in the simplified step-wise protocol of Examples 2, 5, 7) or the nested PCR using primers PX1 and PX2 (partial step-wise protocol of Example 3). Thus, the protocol was simplified further.

50 ng of genomic DNA samples (as in Example 7) were amplified with the primers P2'B (or P2'D), P1' and P3' (as in Example 7). 35 cycles under the same cycling conditions as in step 2 of Example 7 were performed. Branch migration and detection steps were carried out exactly as in Example 7.

The results are summarized in the Table 9.

TABLE 9

| Sample | Signal (RLU) |
| --- | --- |
| Blank | 7696 |
| WT1 (+/+) | 34980 |
| WT2 (+/+) | 34790 |
| WT3 (+/+) | 35166 |
| WT4 (+/+) | 32692 |
| WT5 (+/+) | 33846 |
| WT6 (+/+) | 38470 |
| WT7 (+/+) | 36374 |
| ΔF508/ΔF508 homozygote (−/−) | 1824820 |
| WT/ΔF508 heterozygote 1 (+/−) | 447710 |
| WT/ΔF508 heterozygote 2 (+/−) | 812436 |

Example 9

In this example the simplified direct protocol described in Example 8 for the detection of the ΔF508 3-bp deletion was applied to the 4 point mutations in exon 11. Two different pairs of labeled and tailed primers were used to prepare amplicons for branch migration directly from genomic DNA.

Primer P2": 5'-TAGAAGGAAGATGTGCCTTTCA-3' (SEQ ID NO: 14)
P2"D and P2"B: digoxygenin and biotin-labeled P2", respectively.
Primer P1": 5'-ACCATGCTCGAGATTACGAGTTCT-TAACCCACTAGCCATAAA-3' (SEQ ID NO: 15)
Primer P3": 5'-GATCCTAGGCCTCACGTATTTTCTTAA CCCACTAGCCATAAA-3' (SEQ ID NO: 16)
Primer P2'": 5'-TTACATTAGAAGGAAGATGTGCCT-3' (SEQ ID NO: 17) P2'"D and P2'"B: digoxygenin and biotin-labeled P2'", respectively.
Primer P1'": 5'-ACCATGCTCGAGATTACGAGG TGATTCTTAACCCACTAGCCA-3' (SEQ ID NO: 18)
Primer P3'": 5'-GATCCTAGGCCTCACGTATTG TGATTCTTAACCCACTAGCCA-3' (SEQ ID NO: 19)

All primers were from Oligos Etc., Inc., Wilsonville, Oreg.

PCR from genomic DNA, branch migration and detection were carried out exactly as described in Example 8 (37 PCR cycles were performed). The resulting PCR products were 333 bp and 343 bp in length, respectively.

WT1 below was used as the reference sample and amplified with primers P2"D, P1" and P3" or P2'"D, P1'" and P3'", respectively (right and left column, respectively, in Table 10 below).

All the test samples were amplified with primers P2"B, P1" and P3" or P2'"B, P1'" and P3'", respectively (right and left column, respectively, in Table 10 below).

TABLE 10

| Sample | Signal (RLU) | |
| --- | --- | --- |
| Blank | 7384 | 8396 |
| WT1 (+/+) | 45456 | 56210 |
| WT2 (+/+) | 52480 | 49174 |
| WT3 (+/+) | 65172 | 56992 |
| WT4 (+/+) | 30778 | 88682 |
| WT5 (+/+) | 71906 | 63398 |
| G542X/G542X (−/−) | 1797530 | 1148180 |
| G542X/WT (+/−) | 695056 | 473342 |
| G551D/WT(+/−) | 902458 | 499874 |
| G553X/WT(+/−) | 859416 | 571882 |
| G560T/WT(+/−) | 1030630 | 587710 |

In another experiment, the test and the reference genomic DNA samples were co-amplified with a mixture of primers P2"B, P2"D, P1" and P3" (as in the Partial Step-Wise Approach of Example 3, only without any outer primers). The results are summarized in Table 11 below.

TABLE 11

| Sample | Signal (RLU) |
| --- | --- |
| Blank | 7384 |
| WT1 (+/+) | 18166 |
| WT2 (+/+) | 16462 |
| WT3 (+/+) | 20282 |
| WT4 (+/+) | 19106 |
| WT5 (+/+) | 21790 |
| G542X/G542X (−/−) | 640182 |
| G542X/WT (+/−) | 265984 |
| G551D/WT (+/−) | 294094 |
| G553X/WT (+/−) | 302366 |
| G560T/WT (+/−) | 336964 |

Example 10

This example describes the application of the branch migration assay for colony screening in the in vitro mutagenesis experiments. The assay provided a rapid identification of the mutant clones.

E. coli clones of bacterial glucose-6-phosphate dehydrogenase gene (G6PDH) were produced in a manner similar to that described in European Patent Application No. 94 923 147.6. Amplification directly from bacterial clones was performed as follows. A small amount of bacterial cells were picked with a toothpick, and a toothpick was swirled in 50 µl of the PCR reaction mixture. After incubation at 95° C. for 5 min to lyse the cells, 35 PCR cycles were carried out consisting of 30 sec at 94° C., 1 min at 66° C. and 1 min at 72° C. The resulting PCR product was 320 bp in length. The PCR primers were as follows:

Primer P2"": 5'-GTGTGGAATTGTGAGCGGATAA-3' (SEQ ID NO: 20)
P2""D and P2""B: digoxygenin and biotin-labeled P2"", respectively.
Primer P1"": 5'-ACCATGCTCGAGATTACGAGGT GTGCACGGTATGAGAAATGT-3' (SEQ ID NO: 21)
Primer P3"": 5'-GATCCTAGGCCTCACGTATT GTGTGCACGGTATGAGAAATGT-3' (SEQ ID NO: 22)

All primers were from Oligos Etc., Inc., Wilsonville, Oreg.

The reference amplicon was prepared from the purified diluted plasmid containing the wild type G6PDH gene using the primers P2""D, P1"" and P3"". The primers P2""B, P1"" and P3"" were utilized in the colony-PCR to prepare the test amplicons. The test and the reference amplicons were mixed and subjected to branch migration and detection as described in the examples above.

The results of the colony screening are summarized in Table 12 below.

TABLE 12

| Clone | Signal (RLU) |
| --- | --- |
| Blank | 7518 |
| WT1 | 202084 |
| WT2 | 300284 |
| WT3 | 337380 |
| Mutant 1 (GA > TG) | 1345450 |
| Mutant 2 (AAA > TGC) | 1464900 |
| Mutant 3 (GA > TG) | 2106950 |

Example 11

This example describes an assay for the detection of a mutation in a nucleic acid using a set of four universal primers, two of each are 5'-biotin (B)- and digoxigenin (D)-labeled, respectively. These primers were the same as the following primers from Example 10 above: Primer P2"" (SEQ ID NO: 20), P2""D and P2""B: digoxigenin and biotin-labeled P2"", respectively, Primer P1"" (SEQ ID NO: 21) and Primer P3"" (SEQ ID NO: 22).

Two sets of adapter primers, for exon 10 (ADF10 and ADR10), primers AP1 and AP2, respectively, and exon 11 (ADF11 and ADR11), primers AP3 and AP4, respectively, of the cystic fibrosis gene (from genomic DNA samples, Roche Molecular Systems, Alameda Calif.) were used. These adapter primers were as follows:

AP1: 5' GTGTGGAATTGTGAGCGGATAATAGAA GGAAGATGTGCCTTTCA 3' (SEQ ID NO: 23) wherein the underlined portion corresponds to P2"" and the non-underlined portion corresponds to P2" (SEQ ID NO: 14) (Example 9)

AP2: 5' GTGTGCACGGTATGAGAAATGTTTCT TAAC-CCACTAGCCATAAA 3' (SEQ ID NO: 24) wherein the underlined portion corresponds to the 3'-region (nucleotides 21–42) of primers P1"" and P3"" and the non-underlined portion corresponds to the 3'-region (nucleotides 21–42) of primers P1" (SEQ ID NO: 15) (Example 9) and of P3" (SEQ ID NO: 16) (Example 9)

AP3: 5' GTGTGGAATTGTGAGCGGATAACTCAGTTT TCCTGGATTATGCC 3' (SEQ ID NO: 25) wherein the underlined portion corresponds to P2"" and the non-underlined portion corresponds to P2' (SEQ ID NO: 11) (Example 7)

AP4: 5' GTGTGCACGGTATGAGAAATGTCTAACCG ATTGAATATGGAGCC 3' (SEQ ID NO: 26) wherein the underlined portion corresponds to the 3'-region (nucleotides 21–42) of primers P1"" and P3"" and the non-underlined portion corresponds to PX1" (SEQ ID NO: 10) (Example 11)

The initial amplifications with the adapter primers were carried out in a 96-well block of a UNO thermocycler from Biometra, Tampa Fla. After the initial denaturation step (95° C. for 4 min), 30 cycles were performed consisting of 94° C. for 30 sec, 64° C. for 1 min and 72° C. for 1 min.

The resulting 244 bp (exon 10) and 357 bp (exon 11) amplicons were diluted 1:1000, and 1 µl (per 50 µl reaction volume) aliquots of these dilutions were amplified in a second PCR step (step 2) (20 cycles under the same conditions as in step 1) using the mixture of primers P2""B, P2""D, P1"" and P3"" identified above. 0.625 units of either Pfu DNA polymerase per 50 µl were used in both step 1 and step 2. The resulting PCR products were a 264 bp (exon 10) and 377 bp (exon 11) amplicon, respectively.

In Step 3 (branch migration), the samples were heated at 95° C. for 1 min. (denaturation) followed by 30 min. at 65° C. Step 4 (detection) was performed exactly as described in Example 1 above.

As a control, the primers specific for both amplicons were used in the second PCR as follows: exon 10—P2'B, P2'D, P1' and P3' (Example 8) and exon 11—P2"B, P2"D, P1" and P3" (Example 9). ΔF is ΔF508, 542 is G542X, 551 is G551 D, 553 is R553X and 560 is R560T. Both exon 10 and exon 11 mutations were successfully detected using this procedure. The results are summarized in Table 12.

TABLE 12

| | Signal (RLU) | | | |
| --- | --- | --- | --- | --- |
| | exon 10 | | exon 11 | |
| sample | universal | specific | universal | specific |
| WT1 | 85404 | 59812 | 41044 | 23726 |
| WT2 | 58250 | 32162 | 41242 | 21204 |
| WT3 | 60464 | 30446 | 49078 | 21510 |
| ΔF/ΔF | 65640 | 42086 | 39790 | 18926 |
| 542/542 | 64666 | 32188 | 73300 | 39870 |
| WT/542 | 62710 | 39394 | 531954 | 751084 |
| WT/551 | 56124 | 26768 | 823282 | 1100860 |
| WT/553 | 58550 | 28060 | 547434 | 888654 |
| ΔF/560 | 629520 | 804126 | 597640 | 846434 |

Example 12

An equimolar mixture of the following primers (total concentration of each forward and reverse primers 250 nM) was used.

Unmodified Primers:

The unmodified primers used in this Example 12 were described in Example 1 as follows:
P2B: 5'GCCTTTCAAATTCAGATTGAGC 3' (SEQ ID NO: 3) (P2) biotinylated at the 5'-end
P2D: forward primer P2 labeled with digoxygenin at the 5'-end
P1: a reverse primer having a 3'-portion identical with Pa (SEQ ID NO: 4) and an additional 5'-"tail" t1 (underlined) 20 nucleotides long:

5'-<u>ACCATGCTCGAGATTACGAG</u>GACATTTACAGCAA ATGCTTGC-3' (SEQ ID NO: 5)
P3: reverse primer having a 3'-portion identical with Pa and an additional 5'-"tail" t2 (underlined) 20 nucleotides long:
5'-<u>GATCCTAGGCCTCACGTATT</u>GACATTTACAGCA AATGCTTGC-3' (SEQ ID NO: 6)
3'-etheno Modified Oligonucleotides (Modified Oligos):
P2cB, P2cD, P1c and P3c are the same as P2B, P2D, P1 and P3 but with two etheno-dA's followed by unmodified dG at their 3'-ends. These oligonucleotides were also purchased from Oligos, Etc.
P1c: 5'-GCCTTTCAAATTCAGATTGAGC-NN-G 3' where X is etheno-deoxy A (SEQ ID NO: 27)
P2cB: 5'GCCTTTCAAATTCAGATTGAGC-NN-G 3' where X is etheno-deoxy A (SEQ ID NO: 28) biotinylated at the 5'-end
P2cD: 5'GCCTTTCAAATTCAGATTGAGC-NN-G 3' where X is etheno-deoxy A (SEQ ID NO: 29) biotinylated at the 5'-end
5'-GATCCTAGGCCTCACGTATTGACATTTACAGCA AATGCTTGC-NN-G 3' where X is etheno-deoxy A (SEQ ID NO: 30)
Thirty five PCR cycles (30 sec at 94° C., 1 min at 64° C., 1 min at 72° C.) were performed using 50 ng genomic DNA and 0.625 U Pfu polymerase per 50 µl. The hot start procedure using PCR GEM50 wax beads (Perkin Elmer, Norwalk Conn.) was utilized.
Branch Migration:
After completion of PCR as described above, the samples were subjected to branch migration: 95° C., 1 min (denaturation), followed by 65° C., 30 min (branch migration).
Detection:
Detection was carried out in a manner similar to that described in U.S. Pat. No. 5,340,716, the relevant portions of which are incorporated herein by reference. The procedure and amounts of the components were as follows:
A 2 µl aliquot of the reaction mixture from the above branch migration was mixed with 100 µl of the beads suspension (2.5 µg of Sens-Sav beads and 2.5 µg Acc-Ab$_{Dig}$ beads per 100 µl buffer A), incubated at 37° C. for 5 min. The reaction mixture was then irradiated with a 150 watt Xenon lamp for 3 sec (3 cycles of 1 sec illumination and 1 sec waiting time) and the signal was then read.
The results of a typical experiment conducted according to the protocol of this Example 12 were as follows (Table 13):

TABLE 13

| Sample | Control Unmodified primers Signal (RLU) | Invention Modified oligos Signal (RLU) |
| --- | --- | --- |
| WT1 | 71252 | 6522 |
| WT2 | 75088 | 6186 |
| WT3 | 80016 | 7634 |
| WT4 | 80052 | 6998 |
| G542X/WT heterozygote | 235644 | 576452 |
| G551D/WT heterozygote | 193542 | 426382 |
| R553X/WT heterozygote | 158058 | 390062 |
| R560T/WT heterozygote | 187078 | 440826 |

WT1–4 are wild type homozygotes.
The results obtained demonstrate that the use of modified oligonucleotide primers that contain one or more unnatural nucleotides at the 3'-end that do not hybridize to the target sequence, e.g., 3'-etheno modified oligonucleotides, in an assay in accordance with the present invention resulted in an improvement over the same assay using unmodified primers. The wild type signal decreased by an order of magnitude whereas the mutant signal increased by approximately a factor of two with the average signal-to-background ratio increasing from 2.5 (marginal) to 67. Other modified oligonucleotides to be used include, for example, modified oligonucleotides 5'-GCCTTTCAAATTCAGATTGAGC-NN-G-3', where X is:

a) O-6-methyl deoxy G (P1a) (SEQ ID NO: 31)
b) O-4-methyl deoxy T (P1b) (SEQ ID NO: 32)

Example 13

In Example 12, the 3'-etheno modified oligonucleotides were aided by implementation of the standard hot start procedure utilizing wax beads. In this Example 13 the hot start procedure employed in Example 12 was not used. PCR conditions were the same as in Example 12, except that all components of the PCR reactions were mixed together at room temperature or on ice. The results are summarized in Table 14.

TABLE 14

| | Signal (RLU) RT | | Signal (RLU) Ice | |
| --- | --- | --- | --- | --- |
| Sample | Control Unmodified primers | Invention Modified oligos | Control Unmodified primers | Invention Modified oligos |
| WT1 | 97992 | 14988 | 112050 | 8612 |
| WT2 | 112110 | 10566 | 100784 | 9634 |
| G551D/WT | 59828 | 49910 | 99516 | 101016 |
| R553X/WT | 51640 | 45180 | 90592 | 121808 |

When the reactions were assembled at room temperature, the average signal to background ratio of 5.3 was observed with the 3'-etheno modified oligonucleotides as compared to no discrimination between mutant and wild type samples with the unmodified primers (Table 14, left). When the reactions were assembled on ice, the average signal to background ratio increased to 24.2 for the 3'-etheno primers, whereas still no discrimination was observed for the unmodified primers (Table 14, right).

The above results demonstrated that the 3'-5' exonuclease activity of the Pfu polymerase was occurring at room temperature and removed the modified nucleotides from some of the molecules of the modified oligonucleotides before PCR cycling began. To slow this process down, smaller amounts of Pfu polymerase were used. In order to preserve the efficiency and yield of PCR, Pfu polymerase was supplemented with Pfu exo- (from Stratagene, La Jolla Calif.) in which the 3'-5' exonuclease activity is missing. PCR conditions were the same as above, except that 40 cycles were performed. The total amount of polymerase (Pfu+Pfu exo$^-$) per reaction was 0.625 U. To make the conditions maximally unfavorable (to encourage non-specific priming), PCR reactions containing 3'-etheno modified oligonucleotides were left at RT for as long as 30 min prior to starting thermocycling. The results are summarized in Table 15.

TABLE 15

| | Signal (RLU) | | |
|---|---|---|---|
| Sample | Pfu | Pfu exo⁻/Pfu (2:1) | Pfu exo⁻/Pfu (1:1) |
| WT1 | 18970 | 8704 | 14540 |
| WT2 | 18652 | 9234 | 21656 |
| G551D/WT | 103236 | 173964 | 314368 |
| R553X/WT | 75130 | 210706 | 337192 |

The results summarized in Table 15 demonstrated that, when the mixture of two enzymes (Pfu and Pfu exo⁻) was used, the 3'-etheno primers were very effective as judged by a signal to background ratio of about 20 as compared with a signal to background ratio of about 4.5 for Pfu alone.

By employing the method of the present invention in conjunction with the use of modified oligonucleotide primers, an improvement of the signal-to-background ratio in a direct approach as applied to the detection of 4 point mutations in exon 11 of the human CFTR gene was realized as demonstrated by this Example 13.

The above discussion includes certain theories as to mechanisms involved in the present invention. These theories should not be construed to limit the present invention in any way, since it has been demonstrated that the present invention achieves the results described.

The above description and examples fully disclose the invention including preferred embodiments thereof. Modifications of the methods described that are obvious to those of ordinary skill in the art such as molecular biology and related sciences are intended to be within the scope of the claims.

What is claimed is:

1. A method of detecting a mutation within a target nucleic acid sequence, said method comprising:
   (a) amplification of said target sequence by polymerase chain reaction, using primers P1 and P2 to produce an amplicon AA, wherein one of said primers P1 and P2 comprises a label and wherein said primer P1 is comprised of a 3'-end portion Pa that can hybridize with said target sequence and 5-end portion B1 that cannot hybridize with said target sequence,
   (b) extending a primer P3 by chain extension along one strand of amplicon AA to produce a tailed target partial duplex A', wherein said primer P3 is comprised of said 3'-end portion Pa and a 5'-end portion A1 that cannot hybridize to said target sequence or its complement, (c) amplification of a reference nucleic acid sequence, using said primer P2 and said primer P3, by polymerase chain reaction to produce amplicon BB, said reference sequence being identical to said target sequence but lacking a possible mutation, wherein said primer P2 comprises a label when said primer P2 in step (a) above comprises a label and said primer P3 comprises a label when said primer P1 in step (a) above comprises a label, (d) extending said primer P1 by chain extension along one strand of amplicon BB to produce a tailed reference partial duplex B', (e) allowing said tailed target partial duplex A' to bind to said tailed reference partial duplex B', and (f) detecting the binding of one of said labels to another of said labels as a result of the formation of a complex between said tailed partial duplexes, the binding thereof being directly related to the presence of said mutation.

2. The method of claim 1 wherein said amplification of step (c) is carried out in the same reaction medium as that used for step (a).

3. The method of claim 2 wherein said amplification of step (c) is carried out simultaneously with the amplification of step (a).

4. The method of claim 1 wherein the label of primer P2 in step (c) is different than the label of primer P2 in step (a).

5. The method of claim 4 wherein said labels are independently selected from the group consisting of oligonucleotides, enzymes, dyes, fluorescent molecules, chemiluminescers, coenzymes, enzyme substrates, radioactive groups, small organic molecules and solid surfaces.

6. The method of claim 4 wherein said nucleic acid is DNA.

7. A method of preparing a DNA partial duplex having a portion at an end thereof that has two predefined non-complementary single stranded sequences, said method comprising:

(a) combining a medium containing a nucleic acid with a polymerase, nucleoside triphosphates and two primers, wherein one of said primers P3 is extendable along one of said strands of said nucleic acid, said P3 having a 3'-end portion Pa that binds to said one of said strands and a 5'-end portion A1 that does not bind to one of said strands, and the other of said primers P2 is extendable along the other of said strands of said nucleic acid, wherein the extended primer produced by the extension of one of said primers is a template for the other of said primers, (b) subjecting said medium to temperature cycling to extend said primers, and (c) combining said medium with a primer P1 wherein said P1 has said 3'-end portion Pa that binds to said extended primer P2 and a 5'-end portion B1 that does not bind to said extended P2 primer, and (d) subjecting said medium to conditions such that said P1, binds to and is extended along said extended primer P2 to produce only a complement.

8. The method of claim 7 wherein a label is bound to P2 or P1.

9. The method of claim 8 wherein said label is selected from the group consisting of oligonucleotides, enzymes, dyes, fluorescent molecules, chemiluminescers, coenzymes, enzyme substrates, radioactive groups, small organic molecules, polynucleotide sequences and solid surfaces.

10. A method of detecting a target nucleic acid sequence, said method comprising:

(a) amplification of said target sequence by polymerase chain reaction, using primers P1 and P2 to produce an amplicon AA, wherein one of said primers P1 and P2 comprises a label and said primer P1 is comprised of a 3'-end portion Pa that can hybridize with said target sequence and 5'-end portion B1 that cannot hybridize with said target sequence, (b) extending a primer P3 by chain extension along one strand of amplicon AA to produce a tailed target partial duplex A', wherein said primer P3 is comprised of said 3'-end portion Pa and a 5'-end portion A1 that cannot hybridize to said target sequence or its complement, (c) amplification of a reference nucleic acid sequence different than said target nucleic acid sequence, using said primer P2 and said primer P3, by polymerase chain reaction to produce amplicon BB, wherein said primer P2 comprises a label when said primer P2 in step (a) above comprises a label and said primer P3 comprises a label when said primer P1 in step (a) above comprises a label, (d) extending said primer P1 by chain extension along one strand of amplicon BB to produce a tailed reference partial duplex B', (e) allowing said tailed target partial duplex A' to bind to said tailed reference partial duplex B' to form a complex, and (f) detecting the binding of one of said labels to another of said labels as a result of the formation of said complex, the binding thereof being directly related to the presence of said target nucleic acid sequence.

11. The method of claim 10 wherein said target and said reference nucleic acid sequences are identical but for a mutation.

12. The method of claim 10 for detecting a target nucleic acid sequence that does not contain a mutation.

13. A method for detecting the presence of a difference between two related nucleic acid sequences, said method comprising:

(a) producing from said two related nucleic acid sequences a double stranded target nucleic acid sequence and a double stranded reference nucleic acid sequence wherein each strand of said target nucleic acid sequence has a portion introduced therein that is a nucleotide sequence priming site and wherein each strand of said reference nucleic acid sequence has a portion introduced therein that is a nucleotide sequence priming site, (b) producing, from said target nucleic acid sequence using said nucleotide sequence priming sites, a partial duplex A' comprising a fully complementary double stranded nucleic acid sequence containing said target nucleic acid sequence and a second portion wherein one strand of said double stranded sequence has at its 5'-end a portion A1, and the other strand has at its 3' end a portion A2 that does not hybridize with portion A1, (c) producing, from said reference nucleic acid sequence using said nucleotide sequence priming sites, a partial duplex B' comprising said double stranded nucleic acid reference sequence wherein the strand of B' corresponding to the strand of A' comprising said portion A1 has at its 5'-end a portion B1 that is complementary with said A2 and the other strand of said B' has at its 3'-end a portion B2 that is complementary with said A1, (d) subjecting said partial duplexes A' and B' to conditions that permit said duplexes to hybridize to each other wherein, if said related nucleic acid sequences have a difference, a stable complex is formed comprising said partial duplex A' and said partial duplex B', and (e) determining whether said stable complex is formed, the presence thereof indicating the presence of said difference between said two related nucleic acid sequences.

14. The method of claim 13 wherein steps (a), (b) and (c) comprise polymerase chain reaction and wherein said priming sites are introduced into each respective strand of said target nucleic acid sequence and said reference nucleic acid sequence in step (a) using oligonucleotide primers each having a 3'-end portion that hybridizes to a respective strand of said related nucleic acid sequence and a portion 5' of said 3'-end portion that does not hybridize to said strand, wherein said 3' end portions of said oligonucleotide primers are capable of hybridizing to said oligonucleotide primers used in step (b) or step (c).

15. The method of claim 13 wherein one of the strands of said partial duplex A' comprises a label and one of the strands of said partial duplex B' comprises a label wherein said strand comprising said label is unable to hybridize directly to said strand of said partial duplex A' that comprises a label.

16. The method of claim 15 wherein said labels are independently selected from the group consisting of oligonucleotides, enzymes, dyes, fluorescent molecules, chemiluminescers, coenzymes, enzyme substrates, radioactive groups, small organic molecules, polynucleotide sequences and solid surfaces.

17. The method of claim 13 wherein step (a) is carried out in a separate reaction container from that in which steps (b) and (c) are carried out.

18. The method of claim 13 wherein each of said A1 and said A2 comprise 15 to 60 nucleotides.

19. The method of claim 13 wherein said nucleic acid is DNA.

20. A method for detecting the presence of a mutation in a target nucleic acid sequence, said method comprising:

(a) amplification of said target nucleic acid sequence by polymerase chain reaction using primers PX1$i$ and PX2$i$ to produce a target sequence comprising nucleotide sequence priming sites Pa' and P2', (b) amplification of a reference nucleic acid sequence by polymerase chain reaction using primers PX1$i$ and PX2$i$ to produce a reference sequence comprising nucleotide sequence priming sites Pa' and P2', said reference sequence being identical to said target sequence but lacking a possible mutation, (c) amplification of said target sequence produced in step (a) by polymerase chain reaction, using primers P1 and P2 to produce an amplicon AA, wherein said primer P1 is comprised of a 3'-end portion Pa that can hybridize with priming site Pa' of said target sequence and 5'-end portion B1 that cannot hybridize with said target sequence, (d) extending a primer P3 by chain extension along one strand of amplicon AA to produce a tailed target partial duplex A', wherein said primer P3 is comprised of said 3'-end portion Pa and a 5'-end portion A1 that cannot hybridize to said target sequence or its complement, (e) amplification of said reference sequence produced in step (b), using said primer P2 and said primer P3, by polymerase chain reaction to produce amplicon BB, (f) extending said primer P1 by chain extension along one strand of amplicon BB to produce a tailed reference partial duplex B', (g) allowing said tailed target partial duplex A' to bind to said tailed reference partial duplex B', and (h) detecting the formation of a complex between said tailed partial duplexes, the binding thereof being directly related to the presence of said mutation.

21. The method of claim 20 wherein said amplification of step (b) is carried out in the same reaction medium as that used for step (a) and in a different reaction medium from that used for steps (c) and (e).

22. The method of claim 20 wherein said amplification of step (b) is carried out simultaneously with the amplification of step (a).

23. The method of claim 20 wherein in step (c) one of said primers P1 and P2 comprises a label and wherein in step (e) said primer P2 comprises a label when said primer P2 in step (c) comprises a label and said primer P3 comprises a label when said primer P1 in step (c) comprises a label.

24. The method of claim 23 wherein the label of primer P2 in step (e) is different than the label of primer P2 in step (c).

25. The method of claim 24 wherein said labels are independently selected from the group consisting of oligonucleotides, enzymes, dyes, fluorescent molecules, chemiluminescers, coenzymes, enzyme substrates, radioactive groups, small organic molecules and solid surfaces.

26. The method of claim 24 wherein said nucleic acid is DNA.

27. A kit for detecting a mutation in a target nucleic acid, said kit comprising in packaged combination:

(a) a primer P2 that is extendable along one of said strands of said target nucleic acid, (b) a primer P1 comprising a 3'-end portion Pa that binds to, and is extendable along, the other of said strands of said target nucleic acid and a 5'-end portion B1 that does not bind to said target nucleic acid, (c) a primer P3 comprising said 3'-end portion Pa and a portion A1 that is different than said B1 and does not bind to said target nucleic acid, and (d) a pair of primers for amplifying said target and said reference nucleic acids wherein one of said primers has a 3'-end portion that is hybridizable to said target and said reference nucleic acids and a portion 5' thereof that is not hybridizable with said target or said reference nucleic acids and is substantially identical to said primer P2 and the other of said primers has a 3'-end portion that is hybridizable to said target and said reference nucleic acids and a portion 5' thereof that is not hybridizable with said target or said reference nucleic acids and is substantially identical to said 3'-end portion Pa of said primers P1 and P3.

28. The kit of claim 27 which comprises a reference nucleic acid.

29. The kit of claim 27 which comprises:

(a) a polymerase and (b) nucleoside triphosphates.

30. The kit of claim 27 wherein components (a)–(c) are packaged in one container and components (d) are packaged in a separate container.

31. The kit of claim 27 wherein at least one of said primers P1, P2 or P3 comprises a label.

32. The kit of claim 31 wherein said labels are independently selected from the group consisting of oligonucleotides, enzymes, dyes, fluorescent molecules, chemiluminescers, coenzymes, enzyme substrates, radioactive groups, small organic molecules, polynucleotide sequences and solid surfaces.

* * * * *

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:1:

CAACTGTGGT TAAAGCAATA GTGTGATATA TGA    33

(2) INFORMATION FOR SEQ ID NO:2:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:2:

GCACAGATTC TGAGTAACCA TAATCTCTAC CA    32

(2) INFORMATION FOR SEQ ID NO:3:

(i) SEQUENCE CHARACTERISTICS:
      (A) LENGTH: 22 base pairs
      (B) TYPE: nucleic acid
      (C) STRANDEDNESS: single (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:3:

GCCTTTCAAA TTCAGATTGA GC                                                  22

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:4:

GACATTTACA GCAAATGCTT GC                                                  22

(2) INFORMATION FOR SEQ ID NO:5:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:5:

ACCATGCTCG AGATTACGAG GACATTTACA GCAAATGCTT GC                            42

(2) INFORMATION FOR SEQ ID NO:6:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:6:

GATCCTAGGC CTCACGTATT GACATTTACA GCAAATGCTT GC                            42

(2) INFORMATION FOR SEQ ID NO:7:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:7:

CAACTGTGGT TAAAGCAATA GTGT                                              24

(2) INFORMATION FOR SEQ ID NO:8:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:8:

GCACAGATTC TGAGTAACCA TAAT                                              24

(2) INFORMATION FOR SEQ ID NO:9:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:9:

CAAGTGAATC CTGAGCGTGA                                                   20

(2) INFORMATION FOR SEQ ID NO:10:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:10:

```
CTAACCGATT GAATATGGAG CC                                                    22

(2) INFORMATION FOR SEQ ID NO:11:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:11:

CTCAGTTTTC CTGGATTATG CC                                                    22

(2) INFORMATION FOR SEQ ID NO:12:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:12:

ACCATGCTCG AGATTACGAG CTAACCGATT GAATATGGAG CC                              42

(2) INFORMATION FOR SEQ ID NO:13:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:13:

GATCCTAGGC CTCACGTATT CTAACCGATT GAATATGGAG CC                              42

(2) INFORMATION FOR SEQ ID NO:14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO
```

(iv) ANTI-SENSE: NO (v) FRAGMENT TYPE: C-terminal (xi) SEQUENCE DESCRIPTION: SEQ ID NO:14:

TAGAAGGAAG ATGTGCCTTT CA                                                    22

(2) INFORMATION FOR SEQ ID NO:15:

(i) SEQUENCE CHARACTERISTICS:
             (A) LENGTH: 42 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:15:

ACCATGCTCG AGATTACGAG TTCTTAACCC ACTAGCCATA AA                              42

(2) INFORMATION FOR SEQ ID NO:16:

(i) SEQUENCE CHARACTERISTICS:
             (A) LENGTH: 42 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:16:

GATCCTAGGC CTCACGTATT TTCTTAACCC ACTAGCCATA AA                              42

(2) INFORMATION FOR SEQ ID NO:17:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:17:

TTACATTAGA AGGAAGATGT GCCT                                                  24

(2) INFORMATION FOR SEQ ID NO:18:

(i) SEQUENCE CHARACTERISTICS:
             (A) LENGTH: 42 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:18:

ACCATGCTCG AGATTACGAG GTGATTCTTA ACCCACTAGC CA                              42

(2) INFORMATION FOR SEQ ID NO:19:

(i) SEQUENCE CHARACTERISTICS:
            (A) LENGTH: 43 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:19:

GATCCTAGGC CTCACGTATT GTGATTACTT AACCCACTAG CCA                             43

(2) INFORMATION FOR SEQ ID NO:20:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:20:

GTGTGGAATT GTGAGCGGAT AA                                                    22

(2) INFORMATION FOR SEQ ID NO:21:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:21:

ACCATGCTCG AGATTACGAG GTGTGCACGG TATGAGAAAT GT                              42

(2) INFORMATION FOR SEQ ID NO:22:

```
        (i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:22:

GATCCTAGGC CTCACGTATT GTGTGCACGG TATGAGAAAT GT                               42

(2) INFORMATION FOR SEQ ID NO:23:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:23:

GTGTGGAATT GTGAGCGGAT AATAGAAGGA AGATGTGCCT TTCA                             44

(2) INFORMATION FOR SEQ ID NO:24:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:24:

GTGTGCACGG TATGAGAAAT GTTTCTTAAC CCACTAGCCA TAAA                             44

(2) INFORMATION FOR SEQ ID NO:25:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:25:
```

```
GTGTGGAATT GTGAGCGGAT AACTCAGTTT TCCTGGATTA TGCC                      44
```

(2) INFORMATION FOR SEQ ID NO:26:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:26:

```
GTGTGCACGG TATGAGAAAT GTCTAACCGA TTGAATATGG AGCC                      44
```

(2) INFORMATION FOR SEQ ID NO:27:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:27:

```
GCCTTTCAAA TTCAGATTGA GCNNG                                           25
```

(2) INFORMATION FOR SEQ ID NO:28:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:28:

```
GCCTTTCAAA TTCAGATTGA GCNNG                                           25
```

(2) INFORMATION FOR SEQ ID NO:29:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:29:

GCCTTTCAAA TTCAGATTGA GCNNG                                                         25

(2) INFORMATION FOR SEQ ID NO:30:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:30:

GATCCTAGGC CTCACGTATT GACATTTACA GCAAATGCTT GCNNG                                    45

(2) INFORMATION FOR SEQ ID NO:31:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:31:

GCCTTTCAAA TTCAGATTGA GCNNG                                                         25

(2) INFORMATION FOR SEQ ID NO:32:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (xi) SEQUENCE DESCRIPTION: SEQ ID NO:32:

GCCTTTCAAA TTCAGATTGA GCNNG                                                         25